US010526410B2

(12) United States Patent
Bowers et al.

(10) Patent No.: US 10,526,410 B2
(45) Date of Patent: Jan. 7, 2020

(54) ANTIBODIES DIRECTED AGAINST INTERLEUKIN 36 RECEPTOR (IL-36R)

(71) Applicant: AnaptysBio, Inc., San Diego, CA (US)

(72) Inventors: Peter Bowers, San Diego, CA (US); Andrew John McKnight, San Diego, CA (US); David J. King, Encinitas, CA (US); Marco Londei, San Diego, CA (US)

(73) Assignee: AnaptysBio, Inc., San Diego, CA (US)

( * ) Notice: Subject to any disclaimer, the term of this patent is extended or adjusted under 35 U.S.C. 154(b) by 0 days.

(21) Appl. No.: 15/567,045

(22) PCT Filed: Apr. 15, 2016

(86) PCT No.: PCT/US2016/027676
§ 371 (c)(1),
(2) Date: Oct. 16, 2017

(87) PCT Pub. No.: WO2016/168542
PCT Pub. Date: Oct. 20, 2016

(65) Prior Publication Data
US 2018/0094065 A1 Apr. 5, 2018

Related U.S. Application Data

(60) Provisional application No. 62/147,824, filed on Apr. 15, 2015.

(51) Int. Cl.
*C07K 16/28* (2006.01)
*A61P 37/06* (2006.01)
*A61P 29/00* (2006.01)
*A61K 39/395* (2006.01)
*A61K 39/00* (2006.01)

(52) U.S. Cl.
CPC .... *C07K 16/2866* (2013.01); *A61K 39/39533* (2013.01); *A61P 29/00* (2018.01); *A61P 37/06* (2018.01); *A61K 39/395* (2013.01); *A61K 2039/505* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,828,981 | A | 5/1989 | Maggio |
| 5,122,464 | A | 6/1992 | Wilson et al. |
| 5,464,758 | A | 11/1995 | Gossen et al. |
| 5,770,359 | A | 6/1998 | Wilson et al. |
| 5,814,618 | A | 9/1998 | Bujard et al. |
| 6,843,987 | B2 | 1/2005 | Debets et al. |
| 7,112,715 | B2 | 9/2006 | Chambon et al. |
| 8,034,771 | B2 | 10/2011 | Sims et al. |
| 8,481,021 | B2 | 7/2013 | Sims et al. |
| 8,568,992 | B2 | 10/2013 | Walker et al. |
| 8,871,192 | B2 | 10/2014 | Sims et al. |
| 9,023,995 | B2 | 5/2015 | Brown et al. |
| 2009/0093024 | A1 | 4/2009 | Bowers et al. |
| 2011/0159011 | A1 | 6/2011 | Carrier et al. |
| 2011/0287485 | A1 | 11/2011 | Bowers et al. |
| 2013/0236471 | A1 | 9/2013 | Brown et al. |
| 2014/0234330 | A1 | 8/2014 | Budelsky et al. |
| 2014/0271627 | A1 | 9/2014 | Puro |
| 2015/0017123 | A1 | 1/2015 | Sims et al. |
| 2015/0203584 | A1 | 7/2015 | Brown et al. |
| 2016/0137708 | A1 | 5/2016 | Sims et al. |

FOREIGN PATENT DOCUMENTS

| WO | WO 1992/008796 A1 | 5/1992 |
| WO | WO 1994/028143 A1 | 12/1994 |
| WO | WO 2013/098420 A1 | 7/2013 |

OTHER PUBLICATIONS

Vajdos et al. (J Mol Biol. Jul. 5, 2002;320(2):415-28 at 416) (Year: 2002).*
Brown et al. (J Immunol. May 1996;156(9):3285-91) (Year: 1996).*
Cooper et al. (Molecular Immunology, 1994; 31(8):577-584) (Year: 1994).*
Derer et al., "Blockade of IL-36 Receptor Signaling Does Not Prevent from TNF-Induced Arthritis," *PLOS One*, 9(8): e101954 (2014).
Lamacchia et al., "The severity of experimental arthritis is independent of IL-36 receptor signaling," *Arthritis Research & Therapy*, 15(2): (2013).
European Patent Office, Partial Supplementary European Search Report in European Patent Application No. 16780800.5 (dated Oct. 4, 2018).
Altschul et al., *J. Molecular Biol.*, 215(3): 403-410 (1990).
Altschul et al., *Nucleic Acids Res.*, 25(17): 3389-3402 (1997).
Beigert et al., *Proc. Natl. Acad. Sci. USA*, 106(10): 3770-3775 (2009).

(Continued)

*Primary Examiner* — Brian Gangle
*Assistant Examiner* — Andrea K McCollum
(74) *Attorney, Agent, or Firm* — Leydig, Voit & Mayer, Ltd.

(57) ABSTRACT

The invention relates to an isolated immunoglobulin heavy chain polypeptide and an isolated immunoglobulin light chain polypeptide that bind to a protein encoded by the interleukin 36 receptor (IL-36R). The invention provides an IL-36R-binding agent that comprises the aforementioned immunoglobulin heavy chain polypeptide and immunoglobulin light chain polypeptide. The invention also provides related vectors, compositions, and methods of using the IL-36R-binding agent to treat a disorder or disease that is responsive to IL-36R inhibition, such as cancer, an infectious disease, or an autoimmune disease.

28 Claims, 15 Drawing Sheets
Specification includes a Sequence Listing.

(56) References Cited

OTHER PUBLICATIONS

Bhatia et al., *Curr. Oncol. Rep.*, 13(6): 488-497 (2011).
Bird et al., *Science*, 242: 423-426 (1988).
Blumberg et al., *J. Exp. Med.*, 204(11): 2603-2614 (2007).
Blumberg et al., *J. Immunol.*, 185(7):4354-4362 (2010).
Braitbard et al., "Competition between bound and free peptides in an ELISA-based procedure that assays peptides derived from protein digests," *Proteome Science.*, 4(12): (2006).
Brash et al., *Mol. Cell Biol.*, 7: 2031-2034 (1987).
Colbére-Garapin et al., "A new dominant hybrid selective marker for higher eukaryotic cells." *Journal of molecular biology* 150.1 (1981): 1-14.
Conese et al., "Gene therapy progress and prospects: episomally maintained self-replicating systems." *Gene therapy* 11.24 (2004): 1735-1741.
David et al., "Protein iodination with sold state lactoperoxidase" *Biochemistry* 13.5 (1974): 1014-1021.
De Waal et al., *J. Dermatological Treatment*, 22(2): 102-105 (2011).
Dinarello et al., *Nat. Immunol.*, 11(11): 973 (2010).
Fuhrmann-Benzakein et al. "Inducible and irreversible control of gene expression using a single transgene." *Nucleic acids research* 28.23 (2000): e99-e99.
Goeddel, *Gene Expression Technology: Methods in Enzymology*, vol. 185, Academic Press, San Diego, Calif. (1990).
Holliger et al., "Engineered antibody fragments and the rise of single domains." *Nature biotechnology* 23.9 (2005): 1126-1136.
Hou et al., *J. Biochem.*, 144(1): 115-120 (2008).
Hunter et al., "Preparation of Iodine-131 Labelled Human Growth Hormone of High Specific Activity," *Nature*, 194: 495-496 (1962).
Huston et al., "Protein engineering of antibody binding sites: Recovery of specific activity in an anti-digoxin single-chain Fv analogue produced in *Escherichia coli*," *Proc. Natl. Acad. Sci. USA*, 85: 5879-5883 (1988).
Ichii et al., *Laboratory Investigation*, 90(3): 459-475 (2010).
Ignatova, *Microbial Cell Factories*, 4(23): 1-6 (2005).
Indra et al., "Temporally-controlled site-specific mutagenesis in the basal layer of the epidermis: comparison of the recombinase activity of the tamoxifen-inducible Cre-ERT and Cre-ERT2 recombinases." *Nucleic acids research* 27.22 4324-4327 (1999).
Jack et al., *Proc. Natl. Acad. Sci. USA*, 85: 1581-1585 (1988).
Johnston "Biolistic transformation: microbes to mice." *Nature* (London) 346.6286 (1990): 776-777.
Kashmiri et al., *Methods*, 36 (1): 25-34 (2005).
Kent et al., *Science*, 237: 901-903 (1987).
Kitts et al.,Possee. "A method for producing recombinant baculovirus expression vectors at high frequency." *Biotechniques* 14.5 (1993): 810-817.
Köhler et al., "Derivation of specific antibody-producing tissue culture and tumor lines by cell fusion," *Eur. J. Immunol.*, 6: 511-519 (1976).
Kramer et al., "Transgene Control Engineering in Mammalian Cells," *Methods Molecular Biology*, 308: 123-143 (2005).
Lonberg, *Nat. Biotechnol.*, 23(9): 1117-25 (2005).
Lonberg, *Handb. Exp. Pharmacol.*, 181: 69-97 (2008).
Lowy et al., *Cell*, 22: 817-823 (1980).
Luckow et al. "Efficient generation of infectious recombinant baculoviruses by site-specific transposon-mediated insertion of foreign genes into a baculovirus genome propagated in *Escherichia coli*." *Journal of virology* 67.5 (1993): 4566-4579.
Luckow "Baculovirus systems for the expression of human gene products." *Current opinion in biotechnology* 4.5 (1993): 564-572.
Marrakchi et al., *N. Engl. J. Med.*, 365(7):620-628 (2011).
Mulligan et al., *Proc. Natl. Acad. Sci. USA*, 78: 2072-2076 (1981).
Naik et al., *Dermatologic Clinics*, 31(3): 405-425 (2013).
No et al., *Proc. Natl. Acad. Sci.*, 93: 3346-3351 (1996).
Nygren, *Histochem. and Cytochem.*, 30: 407-412 (1982).
O'Hare et al., *Proc. Natl. Acad. Sci. USA*, 78: 1527-1531 (1981).
Osbourn et al., *Nat. Biotechnol.*, 16: 778 (1998).
Pain et al., "Preparation of protein A-peroxidase monoconjugate using a heterobifunctional reagent, and its use in enzyme immunoassays." *Journal of immunological methods* 40.2 (1981): 219-230.
Santerre et al., "Expression of prokaryotic genes for hygromycin B and G418 resistance as dominant-selection markers in mouse L cells." *Gene* 30.1 (1984): 147-156.
Söding, "Protein homology detection by HMM-HMM comparison." *Bioinformatics* 21.7 (2005): 951-960.
Sugiura et al., *J. Invest. Derm.*, 133(11): 2514-2521 (2013).
Szybalska et al., *Proc. Natl. Acad. Sci. USA*, 48: 2026-2034 (1962).
Tortola et al., *J. Clin. Invest.*, 122(11): 3965-3976 (2012).
Towne et al., *J. Biol. Chem.*, 279(14): 13677-13688 (2004).
Towne et al., *Curr. Opin. Pharmacol.*, 12(4): 486-490 (2012).
Urlaub et al., *Proc. Natl. Acad. Sci. USA*, 97: 4216-4220 (1980).
Vigne et al., *Blood*, 118(22): 5813-5823 (2011).
Vigne et al., *Blood*, 120(17): 3478-3487 (2012).
Wigler et al., *Cell*, 11: 223-232 (1977).
Wigler et al., *Proc. Natl. Acad. Sci. USA*, 77: 3567-3570 (1980).
Wolf et al., "Anti-IL-36R antibodies, potentially useful for the treatment of psoriasis: a patent evaluation of WO2013074569," *Expert Opin. Ther. Patents*, 24(4): 477-479 (Jan. 24, 2014).
Zola, *Monoclonal Antibodies: A Manual of Techniques*, CRC Press, Inc. (1987).
U.S. Patent and Trademark Office, International Search Report and Written Opinion in International Application No. PCT/US2016/027676 (dated Sep. 16, 2016).

\* cited by examiner

10,526,410 B2

ANTIBODIES DIRECTED AGAINST INTERLEUKIN 36 RECEPTOR (IL-36R)

Incorporated by reference in its entirety herein is a computer-readable nucleotide/amino acid sequence listing submitted concurrently herewith and identified as follows: One 70,258 Byte ASCII (Text) file named "723558_ST25.TXT," created on Apr. 13, 2016.

BACKGROUND OF THE INVENTION

The interleukin 36 (IL-36) cytokines IL-36α, IL-36β, and IL-36γ (formerly IL-1F6, IL-1F8, and IL-1F9) are interleukin-1 (IL-1) family members that bind to the IL-36 receptor (IL-36R) (formerly IL-1Rrp2 or IL-1RL2) and use IL-1 receptor accessory protein (IL-1RAcP) as a coreceptor to stimulate intracellular signals similar to those induced by IL-1 (Towne et al., *J. Biol. Chem.,* 279(14): 13677-13688 (2004)). IL-1F5 is an IL-1 family member that has been shown to act as an antagonist of IL-36R, and is now referred to as IL-36Ra (Dinarello et al., *Nat. Immunol.,* 11(11): 973 (2010)).

IL-36α, IL-36β, and IL-36γ are highly expressed in several tissues, including internal epithelial tissues that have been exposed to pathogens, and in skin. Expression of IL-36Ra and IL-36α is significantly up-regulated in IL-1β/TNF-α-stimulated human keratinocytes, and IL-36Rα and IL-36γ mRNAs are overexpressed in psoriasis skin lesions. Elevated IL-36α mRNA and protein expression also have been observed in chronic kidney disease (Ichii et al., Lab Invest., 90(3): 459-475 (2010)). Both murine bone marrow-derived dendritic cells (BMDCs) and CD4+ T lymphocytes constitutively express IL-36R and respond directly to IL-36α, IL-36β, and IL-36γ by producing proinflammatory cytokines (e.g., IL-12, IL-1β, IL-6, TNF-α, and IL-23) inducing a more potent stimulatory effect than other IL-1 cytokines (Vigne et al., *Blood,* 118(22): 5813-5823 (2011)).

Transgenic mice overexpressing IL-36α in keratinocytes exhibit a transient inflammatory skin disorder at birth that renders mice highly susceptible to a 12-O-tetradecanoyl-phorbol 13-acetate-induced skin pathology resembling human psoriasis (Blumberg et al., *J. Exp. Med.,* 204(11): 2603-2614 (2007); and Blumberg et al., *J. Immunol.,* 185 (7):4354-4362 (2010)). Furthermore, IL-36R-deficient mice are protected from imiquimod-induced psoriasiform dermatitis (Tortola et al., *J. Clin. Invest.,* 122(11): 3965-3976 (2012)). These results strongly suggest a role for IL-36 in certain inflammatory disorders of the skin.

IL-36 cytokines also have been implicated in certain severe forms of psoriasis, including pustular psoriasis, generalized pustular psoriasis (GPP), and palmo-plantar pustulosis (PPP)) (see, e.g., Town, J. E. and Sims, J. E., *Curr. Opin. Pharmacol.,* 12(4): 486-90 (2012); and Naik, H. B. and Cowen, E. W., *Dermatol Clin.,* 31(3): 405-425 (2013)). Pustular psoriasis is a rare form of psoriasis characterized by white pustules surrounded by red skin. Generalized pustular psoriasis is a severe, systemic form of pustular psoriasis that has a high risk of fatality, while palmo-plantar pustulosis is a chronic form of pustular psoriasis that affects the palms and soles of the feet. Current treatments for pustular psoriasis, GPP, and PPP include oral retinoids and topical steroids, but these treatments exhibit poor efficacy and severe side effects.

There is a need for antagonists of IL-36R (e.g., an antibody) that bind IL-36R with high affinity and effectively neutralize IL-36R activity. The invention provides such IL-36R-binding agents.

BRIEF SUMMARY OF THE INVENTION

The invention provides an isolated immunoglobulin light chain polypeptide which comprises the amino acid sequence of Gln Val Gln Xaa1 Xaa2 Gln Ser Gly Ala Glu Val Lys Lys Pro Gly Ala Ser Val Lys Val Ser Cys Lys Ala Ser Gly Phe Thr Phe Thr Ser Tyr Asp Ile Asn Trp Val Arg Gln Ala Pro Gly Gln Xaa3 Leu Glu Trp Met Gly Trp Ile Tyr Pro Gly Asp Xaa4 Ser Thr Lys Tyr Asn Glu Lys Phe Lys Gly Arg Val Thr Ile Thr Xaa5 Asp Xaa6 Ser Ala Xaa7 Thr Ala Tyr Met Glu Leu Xaa8 Ser Leu Arg Ser Glu Asp Thr Ala Val Tyr Xaa9 Cys Thr Arg Ser Phe Tyr Thr Met Asp Tyr Trp Gly Gln Gly Thr Thr Val Thr Val Ser Ser (SEQ ID NO: 56), wherein (a) Xaa1 is leucine (Leu) or phenylalanine (Phe), (b) Xaa2 is valine (Val), methionine (Met), or leucine (Leu), (c) Xaa3 is arginine (Arg) or glycine (Gly), (d) Xaa4 is glycine (Gly), serine (Ser), or alanine (Ala), (e) Xaa5 is arginine (Arg) or alanine (Ala), (f) Xaa6 is threonine (Thr) or lysine (Lys), (g) Xaa7 is serine (Ser) or asparagine (Asn), (h) Xaa8 is serine (Ser) or alanine (Ala), and (i) Xaa9 is tyrosine (Tyr) or phenylalanine (Phe).

The invention provides an isolated immunoglobulin heavy chain polypeptide which comprises the amino acid sequence of Gln Val Gln Leu Val Gln Ser Gly Ala Glu Val Lys Lys Pro Gly Ala Ser Val Lys Val Ser Cys Lys Ala Ser Gly Tyr Thr Phe Thr Asn Tyr Xaa1 Met Xaa2 Trp Val Arg Gln Ala Pro Xaa3 Gln Gly Leu Glu Trp Met Gly Met Phe Xaa4 Pro Xaa5 Xaa6 Xaa7 Val Thr Arg Leu Asn Gln Lys Phe Lys Asp Arg Val Thr Met Thr Arg Asp Thr Ser Thr Ser Thr Val Tyr Met Glu Leu Ser Ser Leu Arg Ser Glu Asp Thr Ala Val Tyr Tyr Cys Ala Arg Thr Thr Ser Met Ile Ile Gly Gly Phe Ala Tyr Trp Gly Gln Gly Thr Leu Val Thr Val Ser Ser (SEQ ID NO: 15), wherein (a) Xaa1 is tryptophan (Trp) or tyrosine (Tyr), (b) Xaa2 is histidine (His), asparagine (Asn), or tyrosine (Tyr), (c) Xaa3 is glycine (Gly) or arginine (Arg), (d) Xaa4 is aspartic acid (Asp), glutamic acid (Glu), or histidine (His), (e) Xaa5 is serine (Ser), threonine (Thr), or tyrosine (Tyr), (f) Xaa6 is asparagine (Asn) or glycine (Gly), and (g) Xaa7 is serine (Ser), alanine (Ala), or aspartic acid (Asp).

The invention provides an isolated immunoglobulin light chain polypeptide which comprises the amino acid sequence of Xaa1 Xaa2 Gln Xaa3 Gln Glu Ser Gly Pro Gly Leu Val Lys Pro Ser Gln Thr Leu Ser Leu Thr Cys Thr Val Xaa4 Xaa5 Tyr Ser Ile Thr Xaa6 Asp Phe Ala Trp Asn Trp Ile Arg Gln Xaa7 Pro Gly Xaa8 Xaa9 Leu Glu Trp Ile Gly Tyr Ile Ser Tyr Ser Gly Asp Thr Asn Tyr Asn Pro Ser Leu Lys Ser Arg Val Thr Ile Xaa10 Xaa11 Asp Thr Ser Lys Asn Gln Phe Ser Leu Lys Leu Ser Ser Val Thr Ala Ala Asp Thr Ala Xaa12 Tyr Xaa13 Cys Ala Ile Arg Gly Pro Tyr Ser Phe Thr Tyr Trp Gly Gln Gly Thr Leu Val Thr Val Ser Ser Xaa14 (SEQ ID NO: 57), wherein Xaa1 is glutamine (Gln) or aspartic acid (Asp); Xaa2 is valine (Val) or leucine (Leu); Xaa3 is leucine (Leu) or phenylalanine (Phe); Xaa4 is threonine (Thr) or serine (Ser); Xaa5 is glycine (Gly) or arginine (Arg); Xaa6 serine (Ser) or alanine (Ala); Xaa7 is proline (Pro) or phenylalanine (Phe); Xaa8 is lysine (Lys) or asparagine (Asn); Xaa9 is glycine (Gly) or lysine (Lys); Xaa10 is serine (Ser) or threonine (Thr); Xaa11 is valine (Val) or arginine (Arg); Xaa12 is threonine (Thr) or valine (Val); Xaa13 is tyrosine (Tyr) or phenylalanine (Phe); and Xaa14 is alanine (Ala) or absent.

The invention provides an isolated immunoglobulin heavy chain polypeptide which comprises the amino acid sequence of SEQ ID NO: 33, SEQ ID NO: 34, or SEQ ID NO: 35.

The invention provides an isolated immunoglobulin light chain polypeptide which comprises the amino acid sequence of Asp Ile Val Met Thr Gln Ser Pro Leu Ser Leu Pro Val Thr Pro Gly Glu Pro Ala Ser Ile Ser Cys Arg Ser Ser Lys Ser Leu Leu His Ser Asn Xaa1 Asn Thr Tyr Leu Tyr Trp Xaa2 Leu Gln Lys Pro Gly Gln Ser Pro Gln Leu Leu Ile Xaa3 Arg Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Met Gln His Leu Glu Tyr Pro Phe Thr Phe Gly Gln Gly Thr Lys Leu Glu Ile Lys (SEQ ID NO: 36), wherein (a) Xaa1 is glycine (Gly) or alanine (Ala), (b) Xaa2 is phenylalanine (Phe) or tyrosine (Tyr), and (c) Xaa3 is tyrosine (Tyr) or serine (Ser).

The invention provides an isolated immunoglobulin light chain polypeptide which comprises the amino acid sequence of Asp Ile Val Met Thr Gln Thr Pro Leu Ser Leu Ser Val Thr Pro Gly Gln Pro Ala Ser Ile Ser Cys Arg Ser Ser Lys Ser Leu Leu His Xaa1 Asn Xaa2 Ile Thr Tyr Phe Tyr Trp Tyr Leu Xaa3 Lys Pro Gly Gln Pro Pro Gln Leu Leu Ile Tyr Gln Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Ala Gln Asn Leu Glu Leu Pro Leu Thr Phe Gly Gly Gly Thr Lys Val Glu Ile Lys (SEQ ID NO: 40), (a)Xaa1 is serine (Ser) or arginine (Arg), (b) Xaa2 is glycine (Gly) or alanine (Ala), and (c) Xaa3 is glutamine (Gln) or histidine (His).

The invention provides an isolated immunoglobulin light chain polypeptide which comprises the amino acid sequence of Asp Ile Gln Met Thr Gln Ser Pro Ser Ser Leu Ser Ala Ser Val Gly Asp Arg Val Thr Ile Thr Cys Arg Ala Ser Gln Xaa1 Ile Asn Asn Tyr Leu Asn Trp Tyr Gln Gln Lys Pro Gly Lys Ala Pro Lys Leu Leu Ile Tyr Tyr Thr Ser Xaa2 Leu His Ser Gly Val Pro Ser Arg Phe Ser Xaa3 Ser Gly Ser Gly Xaa4 Asp Xaa5 Thr Phe Thr Ile Ser Ser Leu Gln Pro Glu Asp Ile Ala Thr Tyr Tyr Cys Gln Gln Gly His Thr Leu Pro Trp Thr Phe Gly Gly Gly Thr Lys Val Glu Ile Lys Xaa6 Xaa7 (SEQ ID NO: 58), wherein (a) Xaa1 is aspartic acid (Asp) or tryptophan (Trp), (b) Xaa2 is arginine (Arg) or methionine (Met), (c) Xaa3 is glycine (Gly), serine (Ser) or proline (Pro), (d) Xaa4 is threonine (Thr) or asparagines (Asn), (e) Xaa5 is phenylalanine (Phe) or tyrosine (Tyr), (f) Xaa6 is arginine (Arg) or absent, and (g) Xaa7 is threonine (Thr) or absent.

The invention provides an isolated immunoglobulin light chain polypeptide which comprises the amino acid sequence of SEQ ID NO: 48, SEQ ID NO: 49, or SEQ ID NO: 50.

In addition, the invention provides isolated or purified nucleic acid sequences encoding the foregoing immunoglobulin polypeptides, vectors comprising such nucleic acid sequences, IL-36R-binding agents comprising the foregoing immunoglobulin polypeptides, nucleic acid sequences encoding such IL-36R-binding agents, vectors comprising such nucleic acid sequences, isolated cells comprising such vectors, compositions comprising such IL-36R-binding agents or such vectors with a pharmaceutically acceptable carrier, and methods of treating a disorder that is responsive to IL-36R inhibition by administering effective amounts of such compositions to mammals.

BRIEF DESCRIPTION OF THE SEVERAL VIEWS OF THE DRAWING(S)

DETAILED DESCRIPTION OF THE INVENTION

Figure 1A:
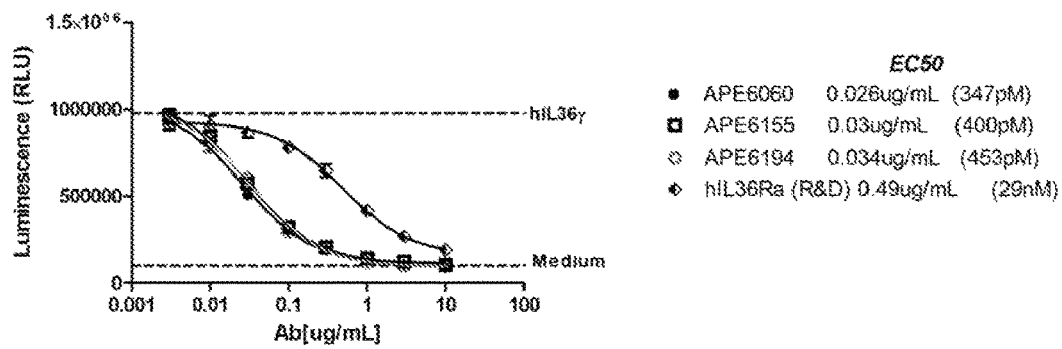
FIG. 1A is a graph depicting the results of the HEK human IL-36R/IL-8 luciferase reporter assay described in Example 1 upon stimulation of cells with hIL-36γ.
Figure 1B:
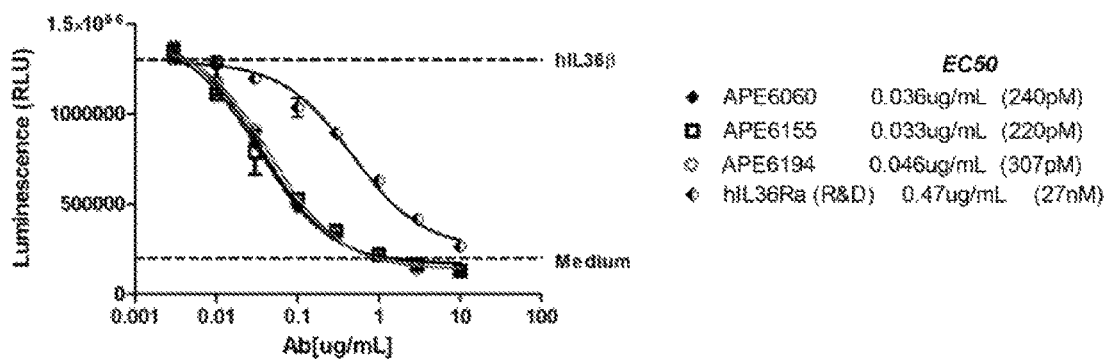
FIG. 1B is a graph depicting the results of the HEK human IL-36R/IL-8 luciferase reporter assay described in Example 1 upon stimulation of cells with hIL-36β.
Figure 1C:
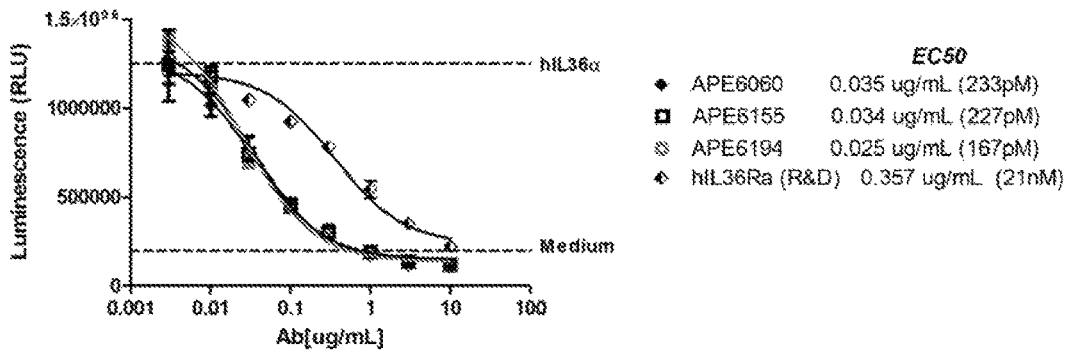
FIG. 1C is a graph depicting the results of the HEK human IL-36R/IL-8 luciferase reporter assay described in Example 1 upon stimulation of cells with hIL-36α.
Figure 1D:
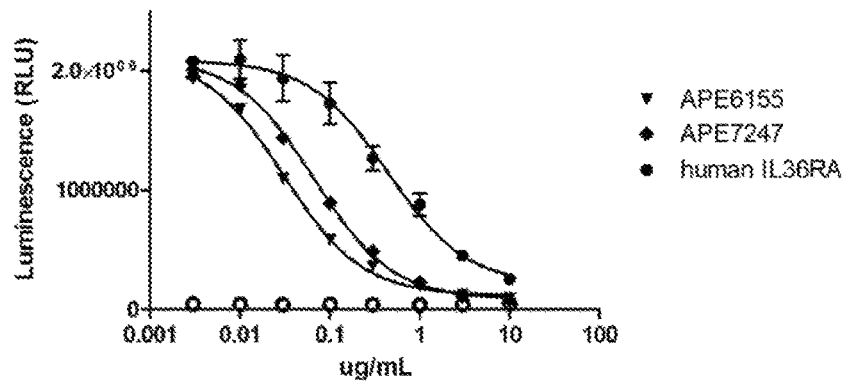
FIG. 1D is a graph depicting the results of the HEK human IL-36R/IL-8 luciferase reporter assay described in Example 1 upon stimulation of cells with 50 ng/mL hIL-36α.
Figure 1E:
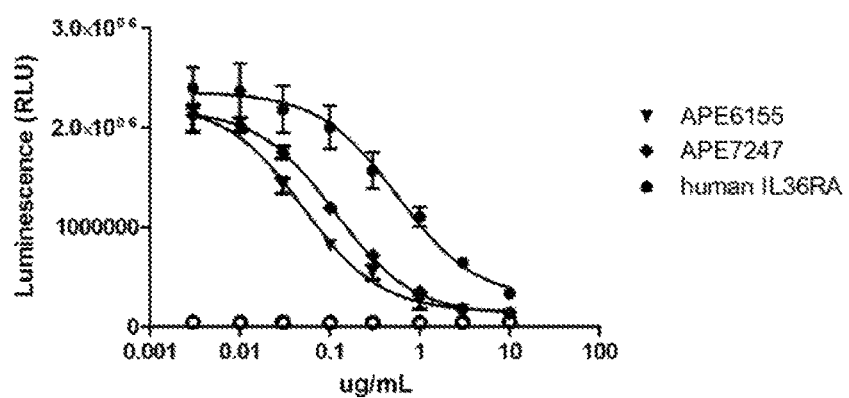
FIG. 1E is a graph depicting the results of the HEK human IL-36R/IL-8 luciferase reporter assay described in Example 1 upon stimulation of cells with 20 ng/mL hIL-36β.
Figure 1F:
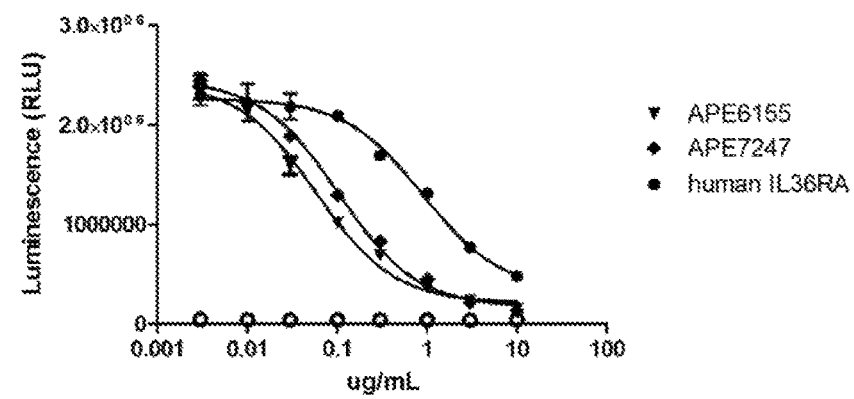
FIG. 1F is a graph depicting the results of the HEK human IL-36R/IL-8 luciferase reporter assay described in Example 1 upon stimulation of cells with 600 ng/mL hIL-36γ.

The invention provides an isolated immunoglobulin heavy chain polypeptide and/or an isolated immunoglobulin light chain polypeptide, or a fragment (e.g., antigen-binding fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. The polypeptide is "isolated" in that it is removed from its natural environment. In a preferred embodiment, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulfide bonds, and the two heavy chains are linked to each other by disulfide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The isolated immunoglobulin heavy chain polypeptide and the isolated immunoglobulin light chain polypeptide of the invention desirably bind to the interleukin 36 receptor (IL-36R), formerly known as IL-1Rrp2. IL-36R is a receptor of the IL-1R family, and binds to the ligands IL-36α (formerly IL-1F6), IL-36β (formerly IL-1F8), and IL-36γ (formerly IL-1F9) (see, e.g., Vigne et al., *Blood,* 118(22): 5813-5823 (2011)). IL-36α, IL-36β, and IL-36γ are members of the IL-1 family of cytokines and bind to IL-36R and use IL-1 receptor accessory protein (IL-1RAcP) as a coreceptor to stimulate intracellular signals similar to those induced by IL-1 (Towne et al., *J. Biol. Chem.,* 279(14): 13677-13688 (2004)). IL-36 cytokines and IL-36R are highly expressed by keratinocytes and other epithelial cell types, as well as dendritic cells and naive CD4+ T-cells (Towne et al., supra; Vigne et al., *Blood,* 118(22): 5813-5823 (2011); and Vigne et al., *Blood,* 120(17): 3478-3487 (2012))

The inventive isolated immunoglobulin heavy chain polypeptide and the inventive isolated immunoglobulin light chain polypeptide can form an agent that binds to IL-36R and another antigen, resulting in a "dual reactive" binding agent (e.g., a dual reactive antibody).

Certain other antibodies which bind to IL-36R, and components thereof, are known in the art (see, e.g., U.S. Patent Publication 2013/0236471). Anti-IL-36R antibodies also are commercially available from sources such as, for example, Abcam (Cambridge, Mass.), and R&D Systems, Inc. (Minneapolis, Minn.).

The invention provides an isolated immunoglobulin light chain polypeptide which comprises, consists of, or consists essentially of the amino acid sequence of Gln Val Gln Xaa1 Xaa2 Gln Ser Gly Ala Glu Val Lys Lys Pro Gly Ala Ser Val Lys Val Ser Cys Lys Ala Ser Gly Phe Thr Phe Thr Ser Tyr Asp Ile Asn Trp Val Arg Gln Ala Pro Gly Gln Xaa3 Leu Glu Trp Met Gly Trp Ile Tyr Pro Gly Asp Xaa4 Ser Thr Lys Tyr Asn Glu Lys Phe Lys Gly Arg Val Thr Ile Thr Xaa5 Asp Xaa6 Ser Ala Xaa7 Thr Ala Tyr Met Glu Leu Xaa8 Ser Leu Arg Ser Glu Asp Thr Ala Val Tyr Xaa9 Cys Thr Arg Ser Phe Tyr Thr Met Asp Tyr Trp Gly Gln Gly Thr Thr Val Thr Val Ser Ser (SEQ ID NO: 56), wherein (a) Xaa1 is leucine (Leu) or phenylalanine (Phe), (b) Xaa2 is valine (Val), methionine (Met), or leucine (Leu), (c) Xaa3 is arginine (Arg) or glycine (Gly), (d) Xaa4 is glycine (Gly), serine (Ser), or alanine (Ala), (e) Xaa5 is arginine (Arg) or alanine (Ala), (f) Xaa6 is threonine (Thr) or lysine (Lys), (g) Xaa7 is serine (Ser) or asparagine (Asn), (h) Xaa8 is serine (Ser) or alanine (Ala), and (i) Xaa9 is tyrosine (Tyr) or phenylalanine (Phe). In some embodiments, the isolated immunoglobulin heavy chain polypeptide comprises, consists of, or consists essentially of the amino acid sequence Gln Val Gln Xaa1 Xaa2 Gln Ser Gly Ala Glu Val Lys Lys Pro Gly Ala Ser Val Lys Val Ser Cys Lys Ala Ser Gly Phe Thr Phe Thr Ser Tyr Asp Ile Asn Trp Val Arg Gln Ala Pro Gly Gln Xaa3 Leu Glu Trp Met Gly Trp Ile Tyr Pro Gly Asp Xaa4 Ser Thr Lys Tyr Asn Glu Lys Phe Lys Gly Arg Val Thr Ile Thr Xaa5 Asp Xaa6 Ser Ala Ser Thr Ala Tyr Met Glu Leu Xaa7 Ser Leu Arg Ser Glu Asp Thr Ala Val Tyr Xaa8 Cys Thr Arg Ser Phe Tyr Thr Met Asp Tyr Trp Gly Gln Gly Thr Thr Val Thr Val Ser Ser (SEQ ID NO: 1), wherein (a) Xaa1 is leucine (Leu) or phenylalanine (Phe), (b) Xaa2 is valine (Val), methionine (Met), or leucine (Leu), (c) Xaa3 is arginine (Arg) or glycine (Gly), (d) Xaa4 is glycine (Gly), serine (Ser), or alanine (Ala), (e) Xaa5 is arginine (Arg) or alanine (Ala), (f) Xaa6 is threonine (Thr) or lysine (Lys), (g) Xaa7 is serine (Ser) or alanine (Ala), and (h) Xaa8 is tyrosine (Tyr) or phenylalanine (Phe).

The inventive heavy chain polypeptide can comprise, consist of, or consist essentially of the amino acid sequence of SEQ ID NO: 56 or SEQ ID NO: 1 with any one of the aforementioned amino acid substitutions in any suitable combination. In one embodiment, the immunoglobulin heavy chain polypeptide comprises, consists of, or consists essentially of an amino acid sequence of any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

The invention also provides an isolated immunoglobulin heavy chain polypeptide that comprises, consists of, or consists essentially of the amino acid sequence Gln Val Gln Leu Val Gln Ser Gly Ala Glu Val Lys Lys Pro Gly Ala Ser Val Lys Val Ser Cys Lys Ala Ser Gly Tyr Thr Phe Thr Asn Tyr Xaa1 Met Xaa2 Trp Val Arg Gln Ala Pro Xaa3 Gln Gly Leu Glu Trp Met Gly Met Phe Xaa4 Pro Xaa5 Xaa6 Xaa7 Val Thr Arg Leu Asn Gln Lys Phe Lys Asp Arg Val Thr Met Thr Arg Asp Thr Ser Thr Ser Thr Val Tyr Met Glu Leu Ser Ser Leu Arg Ser Glu Asp Thr Ala Val Tyr Tyr Cys Ala Arg Thr Thr Ser Met Ile Ile Gly Gly Phe Ala Tyr Trp Gly Gln Gly Thr Leu Val Thr Val Ser Ser (SEQ ID NO: 15), wherein (a) Xaa1 is tryptophan (Trp) or tyrosine (Tyr), (b) Xaa2 is histidine (His), asparagine (Asn), or tyrosine (Tyr), (c) Xaa3 is glycine (Gly) or arginine (Arg), (d) Xaa4 is aspartic acid (Asp), glutamic acid (Glu), or histidine (His), (e) Xaa5 is serine (Ser), threonine (Thr), or tyrosine (Tyr), (f) Xaa6 is asparagine (Asn) or glycine (Gly), and (g) Xaa7 is serine (Ser), alanine (Ala), or aspartic acid (Asp).

The inventive heavy chain polypeptide can comprise, consist of, or consist essentially of the amino acid sequence of SEQ ID NO: 15 with one of the aforementioned amino acid substitutions in any suitable combination. In one embodiment, the immunoglobulin heavy chain polypeptide comprises, consists of, or consists essentially of an amino acid sequence of any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

The invention also provides an isolated immunoglobulin light chain polypeptide which comprises, consists of, or consists essentially of the amino acid sequence of Xaa1 Xaa2 Gln Xaa3 Gln Glu Ser Gly Pro Gly Leu Val Lys Pro Ser Gln Thr Leu Ser Leu Thr Cys Thr Val Xaa4 Xaa5 Tyr Ser Ile Thr Xaa6 Asp Phe Ala Trp Asn Trp Ile Arg Gln Xaa7 Pro Gly Xaa8 Xaa9 Leu Glu Trp Ile Gly Tyr Ile Ser Tyr Ser Gly Asp Thr Asn Tyr Asn Pro Ser Leu Lys Ser Arg Val Thr Ile Xaa10 Xaa11 Asp Thr Ser Lys Asn Gln Phe Ser Leu Lys Leu Ser Ser Val Thr Ala Ala Asp Thr Ala Xaa12 Tyr Xaa13 Cys Ala Ile Arg Gly Pro Tyr Ser Phe Thr Tyr Trp Gly Gln Gly Thr Leu Val Thr Val Ser Ser Xaa14 (SEQ ID NO: 57), wherein Xaa1 is glutamine (Gln) or aspartic acid (Asp); Xaa2 is valine (Val) or leucine (Leu); Xaa3 is leucine (Leu) or phenylalanine (Phe); Xaa4 is threonine (Thr) or serine (Ser); Xaa5 is glycine (Gly) or arginine (Arg); Xaa6 serine (Ser) or alanine (Ala); Xaa7 is proline (Pro) or phenylalanine (Phe); Xaa8 is lysine (Lys) or asparagine (Asn); Xaa9 is glycine (Gly) or lysine (Lys); Xaa10 is serine (Ser) or threonine (Thr); Xaa11 is valine (Val) or arginine (Arg); Xaa12 is threonine (Thr) or valine (Val); Xaa13 is tyrosine (Tyr) or phenylalanine (Phe); and Xaa14 is alanine (Ala) or absent. In some embodiments, the isolated heavy chain immunoglobulin polypeptide comprises, consists of, or consists essentially of the amino acid sequence Xaa1 Val Gln Xaa2 Gln Glu Ser Gly Pro Gly Leu Val Lys Pro Ser Gln Thr Leu Ser Leu Thr Cys Thr Val Xaa3 Gly Tyr Ser Ile Thr Ser Asp Phe Ala Trp Asn Trp Ile Arg Gln Xaa4 Pro Gly Xaa5 Xaa6 Leu Glu Trp Ile Gly Tyr Ile Ser Tyr Ser Gly Asp Thr Asn Tyr Asn Pro Ser Leu Lys Ser Arg Val Thr Ile Xaa7 Xaa8 Asp Thr Ser Lys Asn Gln Phe Ser Leu Lys Leu Ser Ser Val Thr Ala Ala Asp Thr Ala Val Tyr Xaa9 Cys Ala Ile Arg Gly Pro Tyr Ser Phe Thr Tyr Trp Gly Gln Gly Thr Leu Val Thr Val Ser Ser (SEQ ID NO: 25), wherein (a) Xaa1 is glutamine (Gln) or aspartic acid (Asp), (b) Xaa2 is leucine (Leu) or phenylalanine (Phe), (c) Xaa3 is threonine (Thr) or serine (Ser), (d) Xaa4 is proline (Pro) or phenylalanine (Phe), (e) Xaa5 is lysine (Lys) or asparagine (Asn), (f) Xaa6 is glycine (Gly) or lysine (Lys), (g) Xaa7 is serine (Ser) or threonine (Thr), (h) Xaa8 is valine (Val) or arginine (Arg), and (i) Xaa9 is tyrosine (Tyr) or phenylalanine (Phe).

The inventive heavy chain polypeptide can comprise, consist of, or consist essentially of the amino acid sequence of SEQ ID NO: 57 or SEQ ID NO: 25 with one or more of the aforementioned amino acid substitutions in any suitable combination. In one embodiment, the immunoglobulin heavy chain polypeptide comprises, consists of, or consists essentially of an amino acid sequence of any one of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 51, SEQ ID NO: 52, SEQ ID NO: 53, or SEQ ID NO: 54.

In another embodiment, the invention provides an isolated immunoglobulin heavy chain polypeptide which comprises, consists of, or consists essentially of the amino acid sequence of SEQ ID NO: 33, SEQ ID NO: 34, or SEQ ID NO: 35

When the inventive immunoglobulin heavy chain polypeptide consists essentially of an amino acid sequence of any one of SEQ ID NO: 1-SEQ ID NO: 35, additional components can be included in the polypeptide that do not materially affect the polypeptide, e.g., by influencing affinity of the inventive heavy chain polypeptide to IL-36R. Examples of such components include, for example, protein moieties such as biotin that facilitate purification or isolation, passenger mutations, sequences free of problematic sites including free cysteines, additional glycosylation sites, and high-likelihood deamidation or isomerization sites.

When the inventive immunoglobulin heavy chain polypeptide consists of an amino acid sequence of any one of SEQ ID NO: 1-SEQ ID NO: 35, the polypeptide does not comprise any additional components (i.e., components that are not endogenous to the inventive immunoglobulin heavy chain polypeptide).

The invention provides an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 1-SEQ ID NO: 35. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, Algorithms on Strings, Trees and Sequences, Cambridge University Press, Cambridge UK (1997)).

In another embodiment, the invention provides an immunoglobulin light chain polypeptide that comprises, consists of, or consists essentially of the amino acid sequence Asp Ile Val Met Thr Gln Ser Pro Leu Ser Leu Pro Val Thr Pro Gly Glu Pro Ala Ser Ile Ser Cys Arg Ser Ser Lys Ser Leu Leu His Ser Asn Xaa1 Asn Thr Tyr Leu Tyr Trp Xaa2 Leu Gln Lys Pro Gly Gln Ser Pro Gln Leu Leu Ile Xaa3 Arg Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Met Gln His Leu Glu Tyr Pro Phe Thr Phe Gly Gln Gly Thr Lys Leu Glu Ile Lys (SEQ ID NO: 36), wherein (a) Xaa1 is glycine (Gly) or alanine (Ala), (b) Xaa2 is phenylalanine (Phe) or tyrosine (Tyr), and (c) Xaa3 is tyrosine (Tyr) or serine (Ser).

The inventive light chain polypeptide can comprise, consist of, or consist essentially of the amino acid sequence of SEQ ID NO: 36 with one or more of the aforementioned amino acid substitutions in any suitable combination. In one embodiment, the isolated immunoglobulin light chain polypeptide comprises, consists of, or consists essentially of an amino acid sequence of any one of SEQ ID NO: 37, SEQ ID NO: 38, or SEQ ID NO: 39.

The invention also provides an immunoglobulin light chain polypeptide that comprises, consists of, or consists essentially of the amino acid sequence Asp Ile Val Met Thr Gln Thr Pro Leu Ser Leu Ser Val Thr Pro Gly Gln Pro Ala Ser Ile Ser Cys Arg Ser Ser Lys Ser Leu Leu His Xaa1 Asn Xaa2 Ile Thr Tyr Phe Tyr Trp Tyr Leu Xaa3 Lys Pro Gly Gln Pro Pro Gln Leu Leu Ile Tyr Gln Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Ala Gln Asn Leu Glu Leu Pro Leu Thr Phe Gly Gly Gly Thr Lys Val Glu Ile Lys (SEQ ID NO: 40), (a) Xaa1 is serine (Ser) or arginine (Arg), (b) Xaa2 is glycine (Gly) or alanine (Ala), and (c) Xaa3 is glutamine (Gln) or histidine (His).

The inventive light chain polypeptide can comprise, consist of, or consist essentially of the amino acid sequence of SEQ ID NO: 40 with one or more of the aforementioned amino acid substitutions in any suitable combination. In one embodiment, the isolated immunoglobulin light chain polypeptide comprises, consists of, or consists essentially of an amino acid sequence of any one of SEQ ID NO: 41, SEQ ID NO: 42, SEQ ID NO: 43, or SEQ ID NO: 44.

The invention provides an isolated immunoglobulin light chain polypeptide which comprises, consists of, or consists essentially of the amino acid sequence of Asp Ile Gln Met Thr Gln Ser Pro Ser Ser Leu Ser Ala Ser Val Gly Asp Arg Val Thr Ile Thr Cys Arg Ala Ser Gln Xaa1 Ile Asn Asn Tyr Leu Asn Trp Tyr Gln Gln Lys Pro Gly Lys Ala Pro Lys Leu Leu Ile Tyr Tyr Thr Ser Xaa2 Leu His Ser Gly Val Pro Ser Arg Phe Ser Xaa3 Ser Gly Ser Gly Xaa4 Asp Xaa5 Thr Phe Thr Ile Ser Ser Leu Gln Pro Glu Asp Ile Ala Thr Tyr Tyr Cys Gln Gln Gly His Thr Leu Pro Trp Thr Phe Gly Gly Gly Thr Lys Val Glu Ile Lys Xaa6 Xaa7 (SEQ ID NO: 58), wherein (a) Xaa1 is aspartic acid (Asp) or tryptophan (Trp), (b) Xaa2 is arginine (Arg) or methionine (Met), (c) Xaa3 is glycine (Gly), serine (Ser) or proline (Pro), (d) Xaa4 is threonine (Thr) or asparagines (Asn), (e) Xaa5 is phenylalanine (Phe) or tyrosine (Tyr), (f) Xaa6 is arginine (Arg) or absent, and (g) Xaa7 is threonine (Thr) or absent. In some embodiments, the immunoglobulin light chain polypeptide comprises, consists of, or consists essentially of the amino acid sequence Asp Ile Gln Met Thr Gln Ser Pro Ser Ser Leu Ser Ala Ser Val Gly Asp Arg Val Thr Ile Thr Cys Arg Ala Ser Gln Asp Ile Asn Asn Tyr Leu Asn Trp Tyr Gln Gln Lys Pro Gly Lys Ala Pro Lys Leu Leu Ile Tyr Tyr Thr Ser Arg Leu His Ser Gly Val Pro Ser Arg Phe Ser Xaa1 Ser Gly Ser Gly Thr Asp Xaa2 Thr Phe Thr Ile Ser Ser Leu Gln Pro Glu Asp Ile Ala Thr Tyr Tyr Cys Gln Gln Gly His Thr Leu Pro Trp Thr Phe Gly Gly Gly Thr Lys Val Glu Ile Lys (SEQ ID NO: 45), wherein (a) Xaa1 is serine (Ser) or proline (Pro), and (b) Xaa2 is phenylalanine (Phe) or tyrosine (Tyr).

The inventive light chain polypeptide can comprise, consist of, or consist essentially of the amino acid sequence of SEQ ID NO: 58 or SEQ ID NO: 45 with one or more of the aforementioned amino acid substitutions in any suitable combination. In one embodiment, the isolated immunoglobulin light chain polypeptide comprises, consists of, or consists essentially of an amino acid sequence of any one of SEQ ID NO: 46, SEQ ID NO: 47, or SEQ ID NO: 55.

In another embodiment, the invention provides an isolated immunoglobulin light chain polypeptide which comprises, consists of, or consists essentially of the amino acid sequence of SEQ ID NO: 48, SEQ ID NO: 49, or SEQ ID NO: 50

When the inventive immunoglobulin light chain polypeptide consists essentially of an amino acid sequence of any one of SEQ ID NO: 36-SEQ ID NO: 50, additional components can be included in the polypeptide that do not materially affect the polypeptide, such as those described herein. When the inventive immunoglobulin light chain polypeptide consists of an amino acid sequence of any one of SEQ ID NO: 36-SEQ ID NO: 50, the polypeptide does not comprise any additional components (i.e., components that are not endogenous to the inventive immunoglobulin light chain polypeptide).

The invention provides an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 36-SEQ ID NO: 50. Nucleic acid or amino acid sequence "identity" can be determined using the methods described herein.

One or more amino acids of the aforementioned immunoglobulin heavy chain polypeptides and/or light chain polypeptides can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (D or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the aforementioned immunoglobulin heavy chain polypeptides and/or light chain polypeptides. Any number of any suitable amino acids can be inserted into the amino acid sequence of the immunoglobulin heavy chain polypeptide and/or light chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy chain polypeptide and/or light chain polypeptide. Preferably, 1-10 amino acids (e.g., 1, 2, 3, 4, 5, 6, 7, 8, 9, or 10 amino acids) are inserted into the amino acid sequence of the immunoglobulin heavy chain polypeptide and/or light chain polypeptide. In this respect, the amino acid(s) can be inserted into any one of the aforementioned immunoglobulin heavy chain polypeptides and/or light chain polypeptides in any suitable location. Preferably, the amino acid(s) are inserted into a CDR (e.g., CDR1, CDR2, or CDR3) of the immunoglobulin heavy chain polypeptide and/or light chain polypeptide.

The inventive isolated immunoglobulin heavy chain polypeptide and light chain polypeptides are not limited to polypeptides comprising the specific amino acid sequences described herein. Indeed, the immunoglobulin heavy chain polypeptide or light chain polypeptide can be any heavy chain polypeptide or light chain polypeptide that competes with the inventive immunoglobulin heavy chain polypeptide or light chain polypeptide for binding to IL-36R. In this respect, for example, the immunoglobulin heavy chain polypeptide or light chain polypeptide can be any heavy chain polypeptide or light chain polypeptide that binds to the same epitope of IL-36R recognized by the heavy and light chain polypeptides described herein. Antibody competition can be assayed using routine peptide competition assays which utilize ELISA, Western blot, or immunohistochemistry methods (see, e.g., U.S. Pat. Nos. 4,828,981 and 8,568,992; and Braitbard et al., *Proteome Sci.*, 4: 12 (2006)).

The invention provides an IL-36R-binding agent comprising, consisting essentially of, or consisting of one or more of the inventive isolated amino acid sequences described herein. By "IL-36R-binding agent" is meant a molecule, preferably a proteinaceous molecule, which binds specifically to the IL-36R protein. Preferably, the IL-36R-binding agent is an antibody or a fragment (e.g., antigen-binding fragment) thereof. The IL-36R-binding agent of the invention comprises, consists essentially of, or consists of the inventive immunoglobulin heavy chain polypeptide and/or the inventive immunoglobulin light chain polypeptide. In one embodiment, the IL-36R-binding agent comprises, consists essentially of, or consists of the inventive immunoglobulin heavy chain polypeptide or the inventive immunoglobulin light chain polypeptide. In another embodiment, the IL-36R-binding agent comprises, consists essentially of, or consists of the inventive immunoglobulin heavy chain polypeptide and the inventive immunoglobulin light chain polypeptide.

Any amino acid residue of the inventive immunoglobulin heavy chain polypeptide and/or the inventive immunoglobulin light chain polypeptide can be replaced, in any combination, with a different amino acid residue, or can be deleted or inserted, so long as the biological activity of the IL-36R-binding agent is not materially diminished (e.g., enhanced or improved) as a result of the amino acid replacements, insertions, and/or deletions.

The "biological activity" of an IL-36R-binding agent refers to, for example, binding affinity for a particular IL-36R epitope, neutralization or inhibition of IL-36R binding to its receptor(s), neutralization or inhibition of IL-36R activity in vivo (e.g., $IC_{50}$), pharmacokinetics, and cross-reactivity (e.g., with non-human homologs or orthologs of the IL-36R protein, or with other proteins or tissues). In certain embodiments the inventive interleukin 36 receptor (IL-36R)-binding agent desirably exhibits one or more of the following biological activities: (a) inhibits the interaction between IL-36R and IL-36α, IL-36β, and/or IL-36γ, (b) inhibits intracellular signaling mediated by IL-36R, and/or (c) cross-reacts with and inhibits the activity of human and non-human primate (e.g., cynomolgus) IL-36R. Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of a IL-36R-binding agent, refer to the ability to substantially antagonize, prohibit, prevent, restrain, slow, disrupt, alter, eliminate, stop, or reverse the progression or severity of, for example, the biological activity of IL-36R, or a disease or condition associated with IL-36R. The IL-36R-binding agent of the invention preferably inhibits or neutralizes the activity of IL-36R by at least about 20%, about 30%, about 40%, about 50%, about 60%, about 70%, about 80%, about 90%, about 95%, about 100%, or a range defined by any two of the foregoing values.

The IL-36R-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., *Nat. Biotech.*, 23(9): 1126-1129 (2005)). The IL-36R-binding agent can contain any IL-36R-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a F(ab')$_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')$_2$ fragment using mild reducing conditions, (v) a disulfide-stabilized Fv fragment (dsFv), and (vi) a domain antibody (dAb), which is an antibody single variable region domain (VH or VL) polypeptide that specifically binds antigen.

In embodiments where the IL-36R-binding agent comprises a fragment of the immunoglobulin heavy chain or light chain polypeptide, the fragment can be of any size so long as the fragment binds to, and preferably inhibits the activity of, IL-36R. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the IL-36R-binding agent is an antibody or antibody fragment, the antibody or antibody fragment desirably comprises a heavy chain constant region ($F_c$) of any suitable class. Preferably, the antibody or antibody fragment comprises a heavy chain constant region that is based upon wild-type IgG1, IgG2, or IgG4 antibodies, or variants thereof. It will be appreciated that each antibody class, or isotype, engages a distinct set of effector mechanisms for disposing of or neutralizing antigen once recognized. As such, in some embodiments, when the IL-36R-binding agent is an antibody or antibody fragment, it can exhibit one or more effector functions, such as participation in antibody-dependent complement-mediated lysis or antibody-dependent cellular toxicity via interactions with effector molecules and cells (e.g., activation of the complement system).

The IL-36R-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., *Science*, 242: 423-426 (1988); Huston et al., *Proc. Natl. Acad. Sci. USA*, 85: 5879-5883 (1988); and Osbourn et al., *Nat. Biotechnol.*, 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The IL-36R-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The IL-36R-binding agent also can be an antibody conjugate. In this respect, the IL-36R-binding agent can be a conjugate of (1) an antibody, an alternative scaffold, or fragments thereof, and (2) a protein or non-protein moiety comprising the IL-36R-binding agent. For example, the IL-36R-binding agent can be all or part of an antibody conjugated to a peptide, a fluorescent molecule, or a chemotherapeutic agent.

The IL-36R-binding agent can be, or can be obtained from, a human antibody, a non-human antibody, or a chimeric antibody. A "chimeric" antibody is an antibody or fragment thereof comprising both human and non-human regions. Preferably, the IL-36R-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In one embodiment of the invention, CDRH3 of the inventive IL-36R-binding agent is obtained or derived from a mouse monoclonal antibody, while the remaining variable regions and constant region of the inventive IL-36R-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In one embodiment, a humanized antibody can be produced using the methods described in, e.g., U.S. Patent Application Publication 2011/0287485 A1.

In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention provides an IL-36R-binding agent comprising at least one CDR of an immunoglobulin heavy chain and/or light chain polypeptide as described herein. The IL-36R-binding agent can comprise one, two, or three CDRs of an immunoglobulin heavy chain and/or light chain variable region as described herein.

In a preferred embodiment, the IL-36R-binding agent binds an epitope of IL-36R which blocks the binding of IL-36R to any of its ligands (e.g., IL-36α, IL-36β, and IL-36γ) and inhibits IL-36R-mediated signaling. The invention also provides an isolated or purified epitope of IL-36R which blocks the binding of IL-36R to any of its ligands in an indirect or allosteric manner.

The invention also provides one or more isolated or purified nucleic acid sequences that encode the inventive immunoglobulin heavy chain polypeptide, the inventive immunoglobulin light chain polypeptide, and the inventive IL-36R-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The invention further provides a vector comprising one or more nucleic acid sequences encoding the inventive immunoglobulin heavy chain polypeptide, the inventive immunoglobulin light chain polypeptide, and/or the inventive IL-36R-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the inventive immunoglobulin heavy polypeptide, the inventive immunoglobulin light chain polypeptide, and/or the inventive IL-36R-binding agent, the vector preferably comprises expression control sequences, such as promoters, enhancers, polyadenylation signals, transcription terminators, signal peptides (e.g., the osteonectin signal peptide), internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Life Technologies (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviralbased pLP1 from Invitrogen (Carlsbad, Calif.), and the retroviral vectors pFB-ERV plus pCFB-EGSH from Stratagene (La Jolla, Calif.).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive polypeptides alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive polypeptides can be introduced into a host cell that is capable of expressing the polypeptides encoded thereby, including any suitable prokaryotic or eukaryotic cell. As such, the invention provides an isolated cell comprising the inventive vector. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhinosporidium, Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HIS (Invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In one embodiment, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA*, 85: 1581-1585 (1988)), Raji cells (CCL-86), PER.C6 cells (Crucell Holland B.V., Leiden, The Netherlands), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

The invention provides a composition comprising an effective amount of the inventive immunoglobulin heavy chain polypeptide, the inventive immunoglobulin light chain polypeptide, the inventive IL-36R-binding agent, the inventive nucleic acid sequence encoding any of the foregoing, or the inventive vector comprising the inventive nucleic acid sequence. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, IL-36R-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy*, 21st Edition, Lippincott Williams & Wilkins, Philadelphia, Pa. (2001).

The invention further provides a method of treating a disorder in a mammal that is responsive to IL-36R inhibition or neutralization. The method comprises administering the aforementioned composition to a mammal having a disorder that is responsive to IL-36R inhibition or neutralization, whereupon the disorder is treated in the mammal. A disorder that is "responsive to IL-36R inhibition" or "responsive to IL-36R neutralization" refers to any disease or disorder in which a decrease in IL-36R levels or activity has a therapeutic benefit in mammals, preferably humans, or the improper expression (e.g., overexpression) or increased activity of IL-36R causes or contributes to the pathological effects of the disease or disorder. Disorders that are responsive to IL-36R inhibition include, for example, inflammatory diseases, autoimmune diseases, respiratory diseases, metabolic disorders, and cancer.

Inflammatory disorders include, for example, allergic inflammation of the skin, lungs, and gastrointestinal tract, atopic dermatitis (also known as atopic eczema), asthma (allergic and non-allergic), epithelial-mediated inflammation, fibrosis (e.g., idiopathic pulmonary fibrosis, scleroderma, kidney fibrosis, and scarring), allergic rhinitis, food allergies (e.g., allergies to peanuts, eggs, dairy, shellfish, tree nuts, etc.), seasonal allergies, and other allergies.

The inventive method can be used to treat any type of autoimmune disease (i.e., as disease or disorder caused by immune system overactivity in which the body attacks and damages its own tissues), such as those described in, for example, MacKay I. R. and Rose N. R., eds., *The Autoimmune Diseases, Fifth Edition*, Academic Press, Waltham, Mass. (2014). Examples of autoimmune diseases that can be treated by the inventive method include, but are not limited to, multiple sclerosis, asthma, type 1 diabetes mellitus, rheumatoid arthritis, scleroderma, Crohn's disease, psoriasis vulgaris (commonly referred to as psoriasis), pustular psoriasis, generalized pustular psoriasis (GPP), palmo-plantar pustulosis (PPP), inflammatory bowel disease, psoriatic arthritis, multiple sclerosis, rheumatoid arthritis, systemic lupus erythematosus (SLE), ulcerative colitis, and ankylosing spondylitis. In a preferred embodiment, the inventive method is used to treat pustular psoriasis, generalized pustular psoriasis, palmo-plantar pustulosis (PPP), or psoriasis vulgaris.

Pustular psoriasis is a rare form of psoriasis characterized by white pustules surrounded by red skin. Generalized pustular psoriasis (GPP) is a life-threatening disease characterized by sudden, repeated episodes of high-grade fever, generalized rash, and disseminated pustules, with hyperleukocytosis and elevated serum levels of C-reactive protein, which can be caused by a deficiency in the interleukin-36-receptor antagonist (interleukin-36Ra) (Marrakchi et al., *N. Engl. J. Med.*, 365(7):620-628 (2011)). GPP often presents in patients with existing or prior psoriasis vulgaris (PV); however, GPP can develop in patients without a history of PV (Sugiura et al., *J. Invest. Derm.*, 133: 2514-2521 (2013)). Palmo-plantar pustulosis is a chronic inflammatory skin disease characterized by sterile pustules and red, scaly skin on the palms and soles that considerably impairs the quality of life of affected individuals (de Waal, A. C. and van de Kerkhof, P. C. M., *J. Dermatological Treatment*, 22(2): 102-105 (2011)).

Examples of respiratory diseases that can be treated by the inventive method include, but are not limited to, asthma, cystic fibrosis, emphysema, chronic obstructive pulmonary disease (COPD), and acute respiratory distress syndrome. Examples of metabolic disorders that can be treated by the inventive method include, but are not limited to, obesity, type 2 diabetes, atherosclerosis, and cardiovascular disease.

The inventive method can be used to treat any type of cancer known in the art, including but not limited to, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, leukemia, lymphoma, and Merkel cell carcinoma (see, e.g., Bhatia et al., *Curr. Oncol. Rep.*, 13(6): 488-497 (2011)).

Administration of a composition comprising the inventive immunoglobulin heavy chain polypeptide, the inventive immunoglobulin light chain polypeptide, the inventive IL-36R-binding agent, the inventive nucleic acid sequence encoding any of the foregoing, or the inventive vector comprising the inventive nucleic acid sequence induces an immune response in a mammal. An "immune response" can entail, for example, antibody production and/or the activation of immune effector cells (e.g., T-cells).

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the IL-36R-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the IL-36R-binding agent to elicit a desired response in the individual. For example, a therapeutically effective amount of an IL-36R-binding agent of the invention is an amount which decreases IL-36R bioactivity in a human.

Alternatively, the pharmacologic and/or physiologic effect may be prophylactic, i.e., the effect completely or partially prevents a disease or symptom thereof. In this respect, the inventive method comprises administering a "prophylactically effective amount" of the IL-36R-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs, or alternatively, the treatment can be continued for the lifetime of the patient. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive IL-36R-binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive IL-36R-binding agent can be measured by any suitable method known in the art. For example, the biological activity can be assessed by determining the stability of a particular IL-36R-binding agent. In one embodiment of the invention, the IL-36R-binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the IL-36R-binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the IL-36R-binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The stability of the inventive IL-36R-binding agent can be measured in terms of the transition mid-point value ($T_m$), which is the temperature where 50% of the amino acid sequence is in its native confirmation, and the other 50% is denatured. In general, the higher the $T_m$, the more stable the protein. In one embodiment of the invention, the inventive IL-36R binding agent comprises a transition mid-point value ($T_m$) in vitro of about 60-100° C. For example, the inventive IL-36R binding agent can comprise a $T_m$ in vitro of about 65-80° C. (e.g., 66° C., 68° C., 70° C., 71° C., 75° C., or 79° C.), about 80-90° C. (e.g., about 81° C., 85° C., or 89° C.), or about 90-100° C. (e.g., about 91° C., about 95° C., or about 99° C.).

The stability of the inventive IL-36R binding agent can be measured using any other suitable assay known in the art, such as, for example, measuring serum half-life, differential scanning calorimetry (DSC), thermal shift assays, and pulse-chase assays. Other methods of measuring protein stability in vivo and in vitro that can be used in the context of the invention are described in, for example, *Protein Stability and Folding*, B. A. Shirley (ed.), Human Press, Totowa, N.J. (1995); *Protein Structure, Stability, and Interactions* (*Methods in Molecular Biology*), Shiver J. W. (ed.), Humana Press, New York, N.Y. (2010); and Ignatova, *Microb. Cell Fact.*, 4: 23 (2005).

The biological activity of a particular IL-36R-binding agent also can be assessed by determining its binding affinity to IL-36R or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In one embodiment, the IL-36R-binding agent can bind to an IL-36R protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the IL-36R-binding agent can bind to IL-36R with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, competitive binding assays, and/or ELISA (see, e.g., Janeway et al. (eds.), *Immunobiology*, 5th ed., Garland Publishing, New York, N.Y., 2001).

The IL-36R-binding agent of the invention may be administered alone or in combination with other drugs. For example, the IL-36R-binding agent can be administered in combination with other agents for the treatment or prevention of the diseases disclosed herein, such as an anti-inflammatory agent including, for example, corticosteroids (e.g., prednisone and fluticasone), non-steroidal anti-inflammatory drugs (NSAIDs) (e.g., aspirin, ibuprofen, and naproxen), biologics (e.g., infliximab (REMICADE™), adalimumab (HUMIRA™), or etanercept (ENBREL™)), methotrexate (MTX), an oral retinoid (e.g. acitretin (SORIATANE™)), and topical steroids.

In addition to therapeutic uses, the IL-36R-binding agent described herein can be used in diagnostic or research applications. In this respect, the IL-36R-binding agent can be used in a method to diagnose a disorder or disease in which the improper expression (e.g., overexpression) or increased activity of IL-36R causes or contributes to the pathological effects of the disease or disorder. In a similar manner, the IL-36R-binding agent can be used in an assay to monitor IL-36R protein levels in a subject being tested for a disease or disorder that is responsive to IL-36R inhibition. Research applications include, for example, methods that utilize the IL-36R-binding agent and a label to detect an IL-36R protein in a sample, e.g., in a human body fluid or in a cell or tissue extract. The IL-36R-binding agent can be used with or without modification, such as covalent or non-covalent labeling with a detectable moiety. For example, the detectable moiety can be a radioisotope (e.g., $^3H$, $^{14}C$, $^{32}P$, $^{35}S$, or $^{125}I$) a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J.*

Immunol. Meth., 40: 219-230 (1981); and Nygren, *J. Histochem. and Cytochem.*, 30: 407-412 (1982)).

IL-36R protein levels can be measured using the inventive IL-36R-binding agent by any suitable method known in the art. Such methods include, for example, radioimmunoassay (RIA), and FACS. Normal or standard expression values of IL-36R can be established using any suitable technique, e.g., by combining a sample comprising, or suspected of comprising, IL-36R with an IL-36R-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of IL-36R polypeptide expressed in a sample is then compared with a standard value.

The IL-36R-binding agent can be provided in a kit, i.e., a packaged combination of reagents in predetermined amounts with instructions for performing a diagnostic assay. If the IL-36R-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

EXAMPLE 1

This example demonstrates that the inventive immunoglobulin heavy chain (HC) and light chain (LC) polypeptides can form antibodies that bind to and block the signaling of human IL-36R in vitro.

HEK293T/17 cells (ATCC CRL-11268) were stably transfected with a plasmid construct encoding either human IL-36R (hIL-36R) or cynomolgus IL-36R (cynoIL-36R) together with an IL-8 promoter (Promega Corp., Madison, Wis.), and a single cell clone was chosen for all subsequent assays.

HEK293 cells were plated at $3\times10^6$ cells/flask onto a T75 culture flask in 10 mL of DMEM+10% FBS and incubated overnight at 37° C. The next morning, 24 µl A FUGENE™ HD (Promega Corporation, Madison, Wis.) was added to 500 µl OPTI-MEM™ medium (Life Technologies, Carlsbad, Calif.) and incubated at room temperature for five minutes. DNA encoding IL-36R (2 µl) and DNA encoding the IL8 promoter (2 µl) were added to the mixture and allowed to incubate for an additional 25 minutes at room temperature. Cynomolgus IL-36R allelic variation was examined by Sanger sequencing, and four distinct allelic variants were identified within cynomolgus monkey populations. HEK cell lines expressing each cynomolgus IL-36R allelic variants were generated separately. For both human and cynomolgus monkey IL-8 reporter cell lines, the endogenously expressed HEK human IL1RAcP was utilized. This DNA/FUGENE™ mixture was gently added to the cells drop-wise for transfection and incubated overnight at 37° C. 24 hours post-transfection, cells were split and placed in hygromycin and puromycin containing DMEM+10% FBS for four weeks for selection. After 4 weeks, stabilized cells were plated at 1 cell/well on a 96-well clear bottom plates (5 plates/cell line). Single cell clones were screened for surface expression of IL-36R and expanded, with low passage number (i.e., 1-3) cells used for the assay described below.

HEK293-human IL36R/IL8 or HEK293-cynoIL36R/IL8 variant stable cell lines were harvested with accutase and seeded with $0.06\times10^6$ cells/well in 100 µl DMEM+10% FBS on a 96-well clear-bottomed plate overnight at 37° C., 5% $CO_2$. The next morning, plates were inverted into the sink to remove media and gently tapped on a paper towel to dry. Diluted antibodies comprising various combinations of the inventive HC and LC polypeptides (see Table 1), IL-36Ra (R&D Systems, Minneapolis, Minn.), and a negative isotype control antibody were prepared in DMEM+10% FBS (Life Technologies, Carlsbad, Calif.) to the desired concentrations by two-fold dilution series, immediately added to the wells (50 µl/well), and allowed to incubate for 20 minutes at 37° C., 5% $CO_2$.

TABLE 1

| Antibody Designation | HC SEQ ID NO: | LC SEQ ID NO: |
|---|---|---|
| APE3798 | 33 | 48 |
| APE4086 | 3 | 38 |
| APE5125/APE5100 | 4 | 39 |
| APE5216 | 5 | 39 |
| APE5281 | 6 | 39 |
| APE5214/APE4881 | 7 | 39 |
| APE5280 | 8 | 39 |
| APE5257 | 9 | 39 |
| APE5258/APE5076 | 10 | 39 |
| APE5212 | 11 | 39 |
| APE5213/5066 | 12 | 39 |
| APE5211 | 13 | 39 |
| APE5217/APE5060 | 14 | 39 |
| APE3849 | 34 | 49 |
| APE3850 | 16 | 41 |
| APE5600 | 18 | 42 |
| APE5598 | 19 | 42 |
| APE5627 | 20 | 42 |
| APE6064 | 21 | 43 |
| APE6060 | 22 | 43 |
| APE6157 | 23 | 43 |
| APE6155/APE6917 | 22 | 44 |
| APE6194 | 24 | 44 |
| APE3847 | 35 | 50 |
| APE5713 | 27 | 47 |
| APE6083 | 32 | 47 |
| APE6903/APE7247 | 52 | 55 |
| APE6904 | 53 | 55 |
| APE6907 | 54 | 55 |

Cells were subsequently stimulated with 50 µl of IL36α, IL36β, or IL36γ ligands (R&D Systems, Minneapolis, Minn.) and allowed to incubate for an additional 24 hours at 37° C., 5% $CO_2$. $EC_{50}$s of each of the individual cytokines were determined empirically prior to the assay. Luciferase activity was determined by using STEADY-GLO™ Luciferase Assay System (Promega, Cat# E2520, Madison, Wis.). 100 µl of 1:1 mix of luciferase assay substrate:buffer was added to each well, incubated for five minutes at room temperature, and transferred (150 ul) onto 96-well black walled, clear bottom plates. Plates were read on ENVISION™ Plate Reader (PerkinElmer, Waltham, Wash.) to determine luminescence (60-sec delay). Data was analyzed using GraphPad PRISM™ Software 5 (GraphPad, San Diego, Calif.).

Figure 2A:
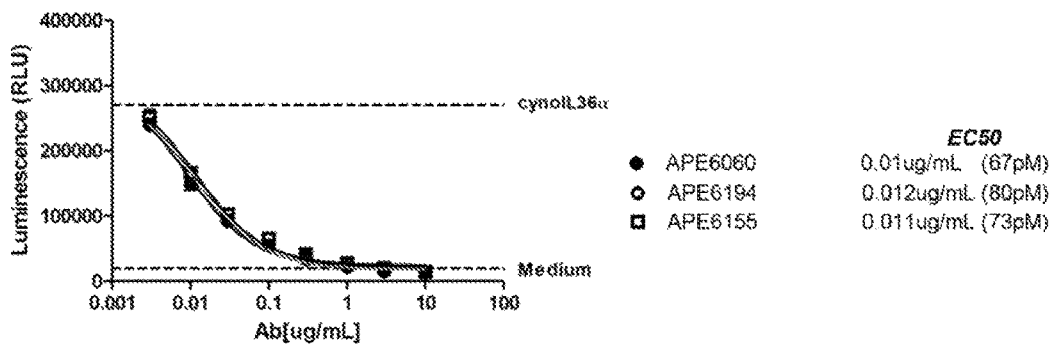
FIG. 2A is a graph depicting the results of the HEK cynomolgus IL-36R/IL-8 luciferase reporter assay described in Example 1 upon stimulation of cells with 2 ug/mL cynoIL-36α.
Figure 2B:
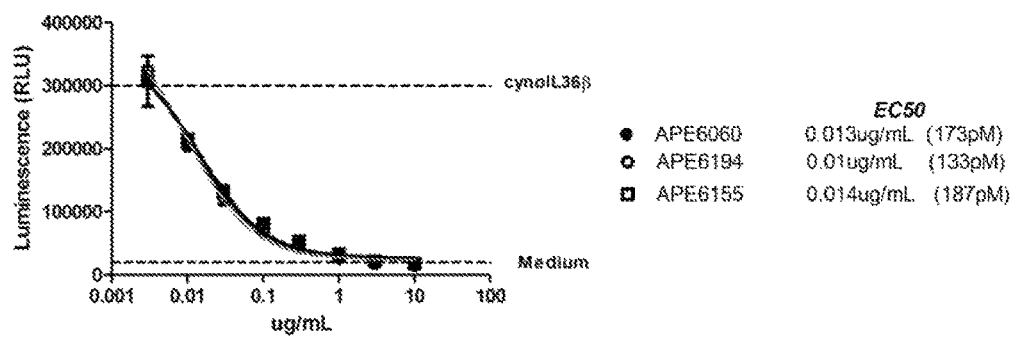
FIG. 2B is a graph depicting the results of the HEK cynomolgus IL-36R/IL-8 luciferase reporter assay described in Example 1 upon stimulation of cells with 10 ug/mL cynoIL-36β.
Figure 2C:
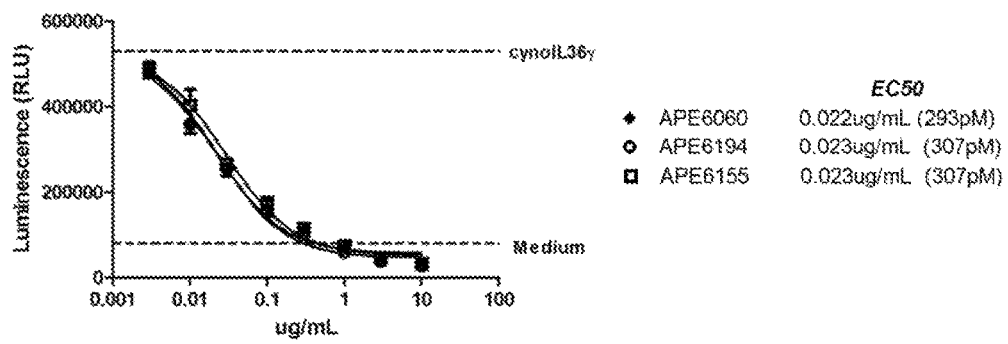
FIG. 2C is a graph depicting the results of the HEK cynomolgus IL-36R/IL-8 luciferase reporter assay described in Example 1 upon stimulation of cells with 300 ng/mL cynoIL-36γ.
Figure 10A:
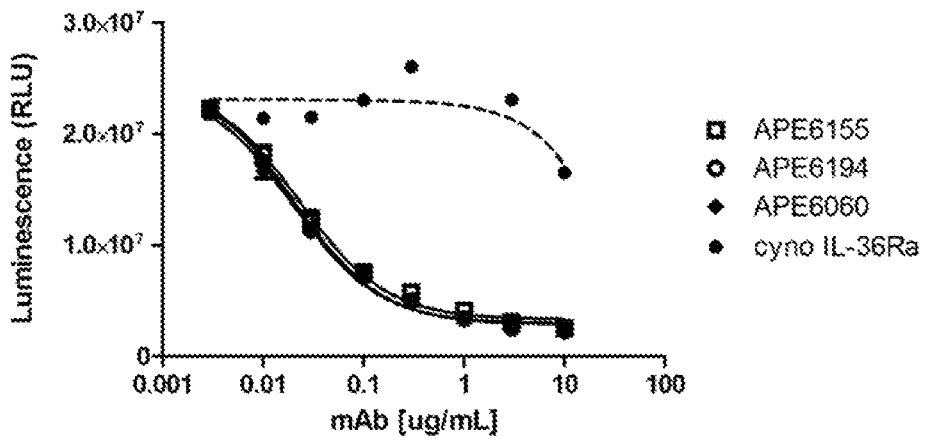
FIG. 10A is a graph depicting the results of the luciferase reporter assay described in Example 1 using HEK cynomolgus IL-36R variant 2 /IL-8 cells stimulated with 20 ng/mL cynoIL-36γ.
Figure 10B:
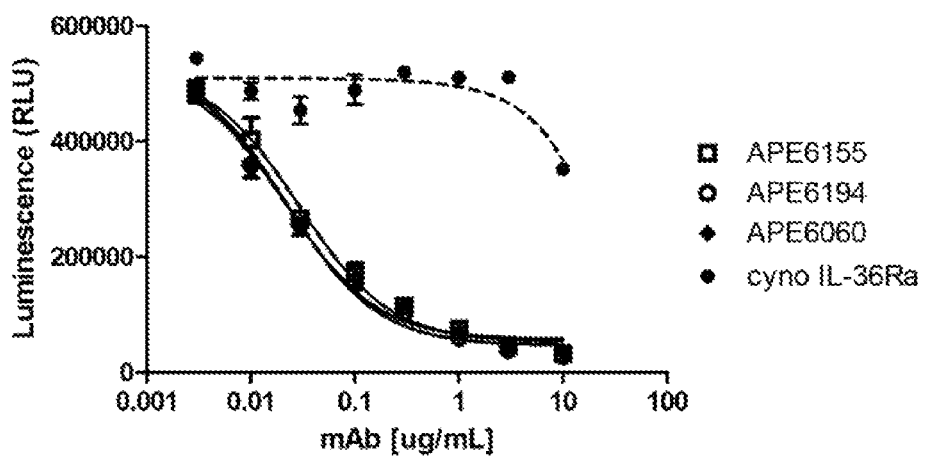
FIG. 10B is a graph depicting the results of the luciferase reporter assay described in Example 1 using HEK cynomolgus IL-36R variant 1/IL-8 cells stimulated with 300 ng/mL cynoIL-36γ.
Figure 10C:
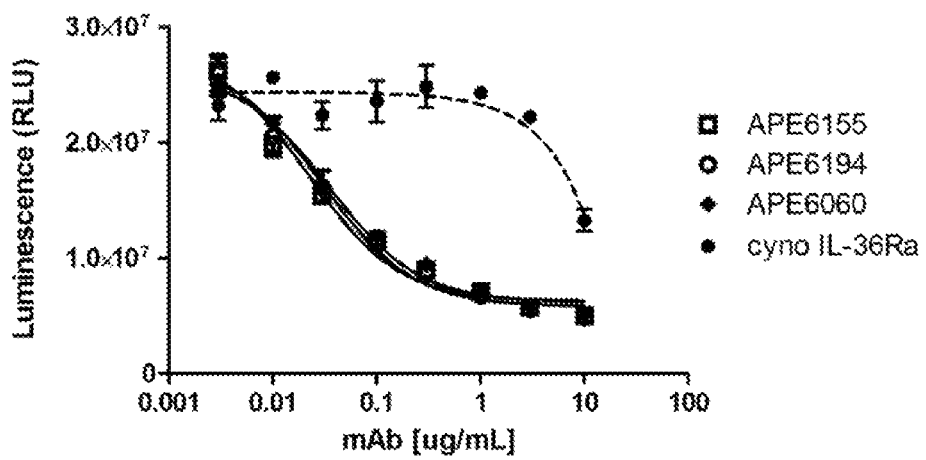
FIG. 10C is a graph depicting the results of the luciferase reporter assay described in Example 1 using HEK cynomolgus IL-36R variant 3/IL-8 cells stimulated with 100 ng/mL cynoIL-36γ.
Figure 10D:
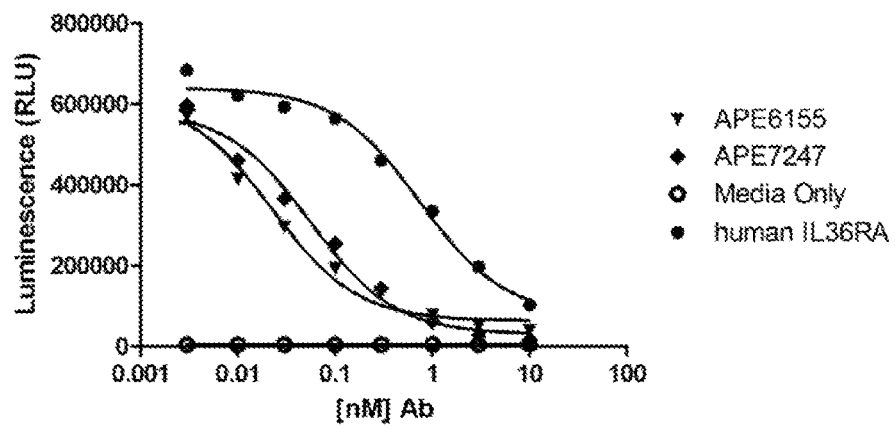
FIG. 10D is a graph depicting the results of the luciferase reporter assay described in Example 1 using HEK cynomolgus IL-36R variant 2/IL-8 cells stimulated with 300 ng/mL cynoIL-36γ.
Figure 10E:
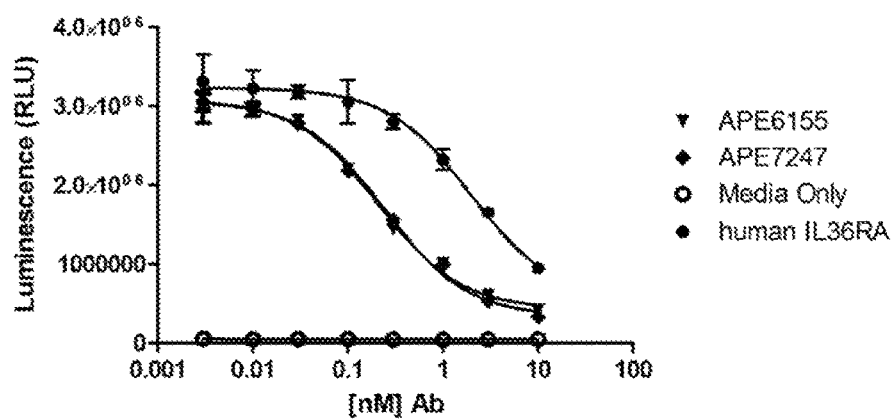
FIG. 10E is a graph depicting the results of the luciferase reporter assay described in Example 1 using HEK cynomolgus IL-36R variant 3/IL-8 cells stimulated with 300 ng/mL cynoIL-36γ.
Figure 10F:
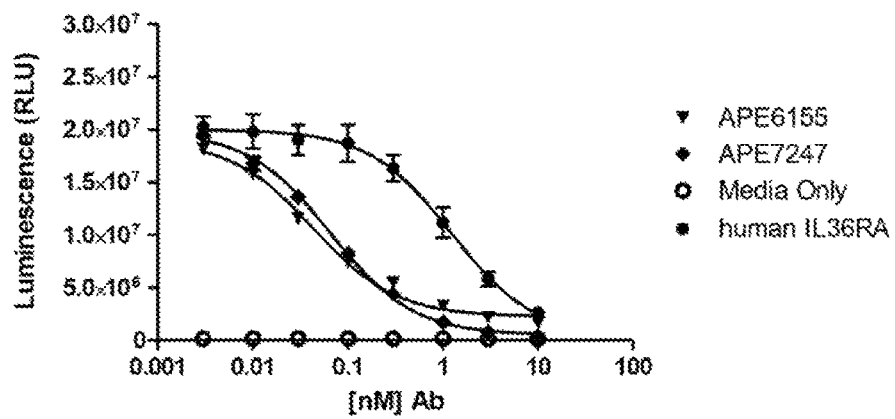
FIG. 10F is a graph depicting the results of the luciferase reporter assay described in Example 1 using HEK cynomolgus IL-36R variant 4/IL-8 cells stimulated with 300 ng/mL cynoIL-36γ.

The results of the IL-8 luciferase reporter assay against human and cyno IL-36R are shown in FIGS. 1A-1F (human IL-36R), FIGS. 2A-2C (cyno IL-36R), FIGS. 10A-10C (cyno IL-36R), and FIGS. 10D-10F (human IL-36R). The measured potencies ($IC_{50}$) of each of the tested antibodies are set forth in Tables 2 and 3.1 and 3.2.

EXAMPLE 2

This example demonstrates that the inventive immunoglobulin heavy chain (HC) and light chain (LC) polypeptides can form antibodies that bind to human IL-36R in vitro.

TABLE 2

HEK human IL-36R IL-8 luciferase reporter assay

| Antibody | HC SEQ ID NO: | LC SEQ ID NO: | EC50 (nM) 50 ng/ml hIL-36α | EC50 (nM) 20 ng/ml hIL-36β | EC50 (nM) 200 ng/ml hIL-36γ |
|---|---|---|---|---|---|
| Chimeric 1D9 (APE3798) | 33 | 48 | | 0.267 | 0.093 |
| Humanized (HzD) 1D9 (APE5281) | 6 | 39 | 0.17 | | 0.12 |
| Chimeric 5D3 (APE3849) | 34 | 49 | | 1.3 | 3.1 |
| Hzd 5D3 (APE6060) | 22 | 43 | 0.23 | 0.24 | 0.35 |
| Hzd 5D3 (APE6155) | 22 | 44 | 0.23 | 0.22 | 0.40 |
| Hzd 5D3 (APE6194) | 24 | 44 | 0.17 | 0.30 | 0.45 |
| Chimeric 18D4 (APE3847) | 35 | 50 | | 4.2 | 3.6 |
| Hzd 18D4 (APE5713) | 27 | 47 | | | 11 |
| Hzd 18D4 (APE7247) | 52 | 55 | .066 | 0.114 | 0.104 |

TABLE 3.1

HEK cyno IL-36R IL-8 luciferase reporter assay

| Antibody | HC SEQ ID NO: | LC SEQ ID NO: | EC50 (nM) 2 µg/ml cIL-36α | EC50 (nM) 10 µg/ml cIL-36β | EC50 (nM) 300 ng/ml cIL-36γ |
|---|---|---|---|---|---|
| Hzd 5D3 (APE6060) | 22 | 43 | 0.067 | 0.17 | 0.29 |
| Hzd 5D3 (APE6155) | 22 | 44 | 0.08 | 0.13 | 0.31 |
| Hzd 5D3 (APE6194) | 24 | 44 | 0.073 | 0.19 | 0.31 |
| Chimeric 18D4 (APE3847) | 35 | 50 | | | 0.51 |
| Hzd 18D4 (APE7247) | 52 | 55 | | | 0.24 |

TABLE 3.2

| Antibody | HC SEQ ID NO: | LC SEQ ID NO: | EC50 (nM) 300 ng/ml IL-36γ (Cyno IL-36R variant 1) | EC50 (nM) 300 ng/ml IL-36γ (Cyno IL-36R variant 2) | EC50 (nM) 300 ng/ml IL-36γ (Cyno IL-36R variant 3) |
|---|---|---|---|---|---|
| Hzd 18D4 (APE7247) | 52 | 55 | 0.079 | 0.065 | 0.42 |
| Hzd 5D3 (APE6155) | 22 | 44 | 0.042 | 0.043 | 0.21 |

The results from this example demonstrate that the inventive immunoglobulin heavy chain (HC) and light chain (LC) polypeptides can form antibodies that bind to and inhibit signaling of human IL-36R in vitro.

DNA samples encoding various immunoglobulin heavy chain (HC) and light chain (LC) polypeptides as described herein were prepared by combining the following: maxi-prepped DNA (containing 6 µg HC plasmid and 6 µg LC plasmid), 1 ml OPTIMEM™ (Life Technologies, Carlsbad, Calif.), and 72 µl FUGENE™ HD Transfection Reagent (Promega, Fitchburg, Wis.). All reagents were pre-warmed. Following thorough mixing and incubation for 25 minutes at room temperature, 1 ml of reagent/DNA mix was added to $8 \times 10^6$ HEK293-c18 cells (ATCC CRL-10852) in each T225 culture flask. 18 hours prior to transfection, the cells were plated in T225 culture flasks with 20 ml of DMEM (Life Technologies, Carlsbad, Calif.) with 10% FBS (Life Technologies, Carlsbad, Calif.) per flask and incubated at 37° C. in 5% $CO_2$ overnight. Following transfection, cells were returned to 37° C. in 5% $CO_2$. The following day, the medium in each flask was exchanged with 25 ml 293 Freestyle medium (Life Technologies, Carlsbad, Calif.), and cells were moved to an incubator at 8% $CO_2$. Antibody production was carried out for 7-12 days. Supernatants were collected from each flask, spun down at 3000 rpm for 10 minutes, and sterile-filtered into fresh tubes.

For antibody purification, approximately 20-30 ml of cell culture supernatants containing the antibodies of interest were passed through a gravity column packed with 1-2 ml MAB SELECT SURE™ LX resin (GE Healthcare, Waukesha, Wis.) pre-equilibrated with PBS buffer (11.9 mM phosphate, 137 mM NaCl, 2.7 mM KCl, pH 7.4) (Fisher Bioreagents, Waltham, Mass.). The column was washed with five column volumes of PBS buffer. Bound antibodies were eluted from the resin with 5-10 column volumes of 0.1 M glycine pH 3.0. The eluate containing the antibodies was concentrated down to an antibody concentration of approximately 0.1-2 mg/mL in Amicon Ultra 10K concentrators (Millipore, Billerica, Mass.), and buffer was exchanged three times against PBS buffer. Antibody concentration was determined on a Nanodrop 2000c spectrophotometer (Thermo Fisher Scientific, Waltham, Mass.), and purity was assessed by SDS-PAGE analysis.

The binding affinities of various purified antibodies comprising immunoglobulin heavy chain (HC) and light chain (LC) polypeptides described herein were evaluated using BIACORE™ T200 (Sapidyne Instruments, Boise, Id.) assays. BIACORE™ T200 evaluation software (GE Healthcare, Buckinghamshire, United Kingdom) is used to determine antibody-antigen binding kinetics and affinity. The extracellular domain of human IL-36R was immobilized at approximately 100 RU onto a CM5 sensor chip (GE Healthcare, Waukesha, Wis.) using amine coupling chemistry. HBS-EP+buffer (0.01 M HEPES, 0.15 M NaCl, 3 mM EDTA, 0.05% Polysorbate, pH 7.6) (Teknova, Hollister, Calif.) was used to reconstitute each antibody at various concentrations Each antibody concentration was then injected for two to three minutes over immobilized antigen at a flow rate of 30 µL/min, and allowed to dissociate for 15 minutes. The surface was regenerated with 60 µL of 3 M $MgCl_2$ after each cycle. Association and dissociation kinetic constants (kon and koff) were fit globally using a 1:1 binding model with mass transport with the BIACORE™ T200 evaluation software in order to report on- and off-rates (ka and kd, respectively), as well as affinities (KD).

The binding affinities of various purified antibodies comprising immunoglobulin heavy chain (HC) and light chain (LC) polypeptides described herein also were evaluated using a KINEXA® 3000 assay(Sapidyne Instruments, Boise, Id.) assays. KINEXA® technology measures the amount of unbound/free antibody molecule in solution phase after incubation with varying concentrations of antigen. Measuring binding events in the solution phase with micro beads for maximized surface area avoids mass transport limitations and mobility effects inherent to methods that measure binding to a solid phase. For each experiment, 50 µg of soluble human or cyno IL-36R extracellular domain was amine-coupled to 50 mg of UltraLink Biosupport beads (Thermo Fisher Scientific, Waltham, Mass.). A constant concentration of antibody (sufficient to produce 0.8 V-1.2 V of signal) was incubated for a sufficient period of time to approach or to reach equilibrium (time of incubation varies for each antibody and is dependent on affinity) with titrated antigen in sample buffer (1× PBS, pH 7.4, 0.02% $NaN_3$, 0.1% BSA). Antibody-antigen solution was then flowed over antigen-coupled beads at a rate of 0.25 mL/min. Free antibody captured by beads was detected using ALEXA FLUOR™ 647-conjugated AffiniPure Donkey Anti-Human IgG (H+L) (Jackson ImmunoResearch, West Grove, Pa.) (500 ng/ml). The KD and/or ABC (active binding concentration) of antibody was obtained from non-linear regression analysis using a one-site homogeneous binding model in the KINEXA™ Pro Software.

Figure 3A:
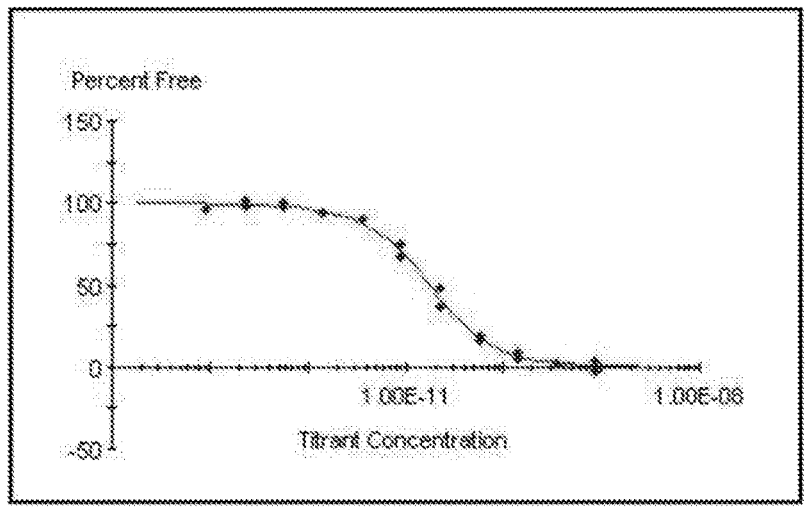
FIG. 3A is a graph depicting experimental data which illustrate the curve for the antibody designated APE5281 binding to human IL-36R as determined by the KINEXA™ assay described in Example 2.
Figure 3B:
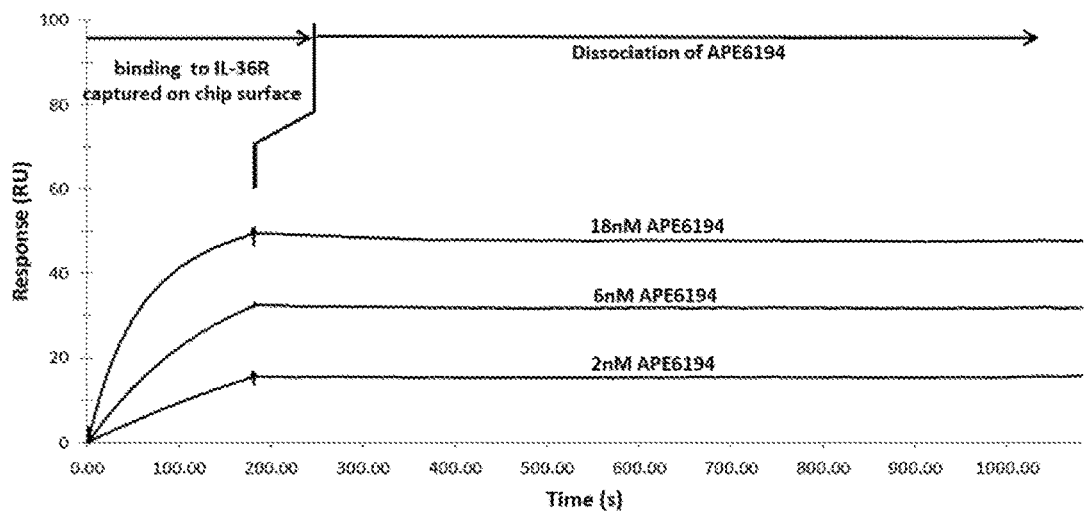
FIG. 3B is a graph depicting experimental data which illustrate the curve for the antibody designated APE6194 binding to human IL-36R as determined by the BIA-CORE™ assay described in Example 2.
Figure 3C:
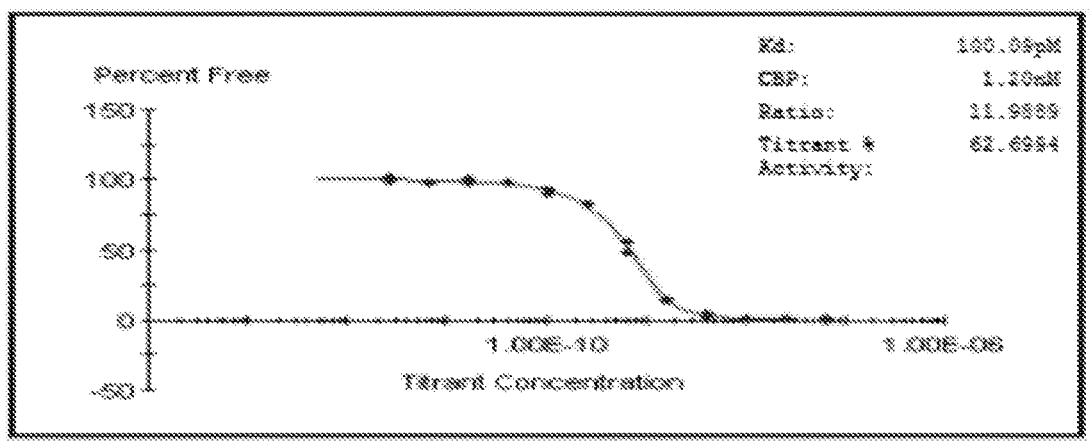
FIG. 3C is a graph depicting experimental data which illustrate the curve for the antibody designated APE7247 binding to human IL-36R as determined by the KINEXA™ assay described in Example 2.
Figure 4A:
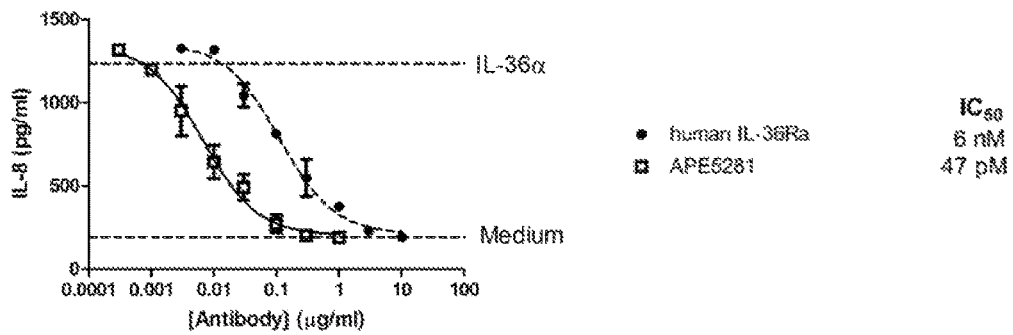
FIG. 4A is a graph depicting the results of the IL-8 secretion assay in primary human keratinocytes described in Example 3 using 10 ng/mL hIL-36α.
Figure 4B:
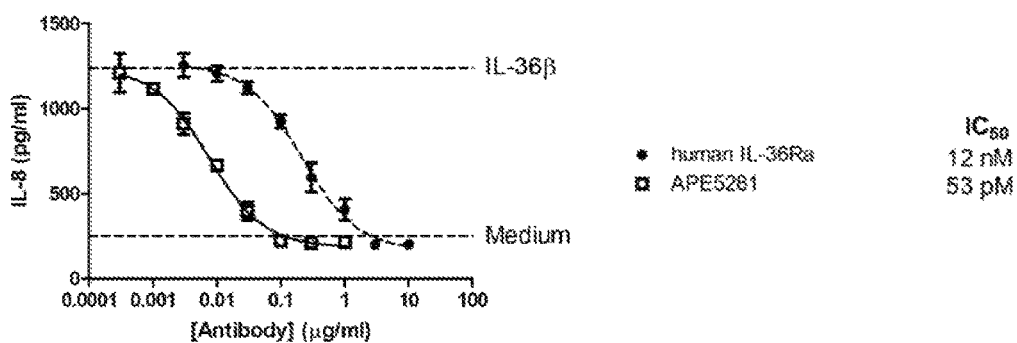
FIG. 4B is a graph depicting the results of the IL-8 secretion assay in primary human keratinocytes described in Example 3 using 1 ng/mL hIL-36β.
Figure 4C:
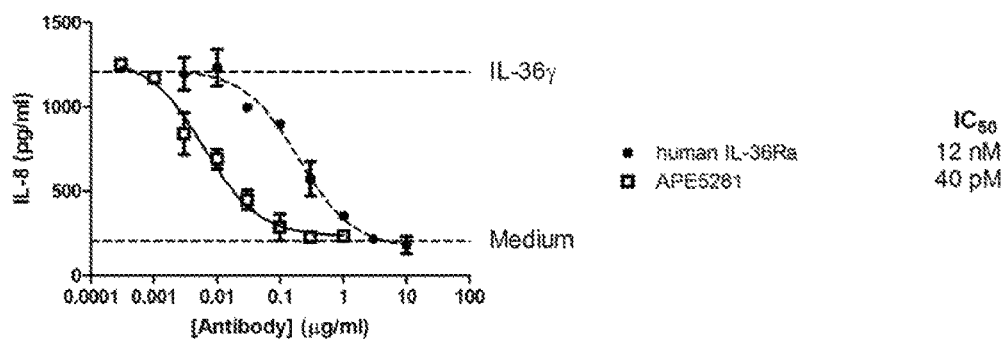
FIG. 4C is a graph depicting the results of the IL-8 secretion assay in primary human keratinocytes described in Example 3 using 100 ng/mL hIL-36γ.
Figure 4D:
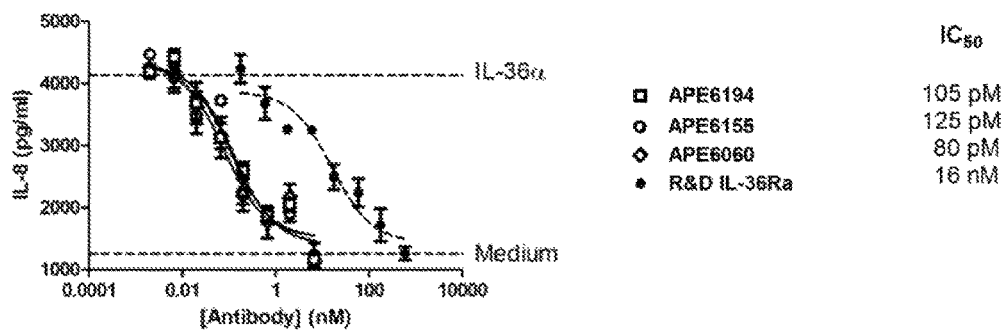
FIG. 4D is a graph depicting the results of the IL-8 secretion assay in primary human keratinocytes described in Example 3 using 10 ng/mL hIL-36α.
Figure 4E:
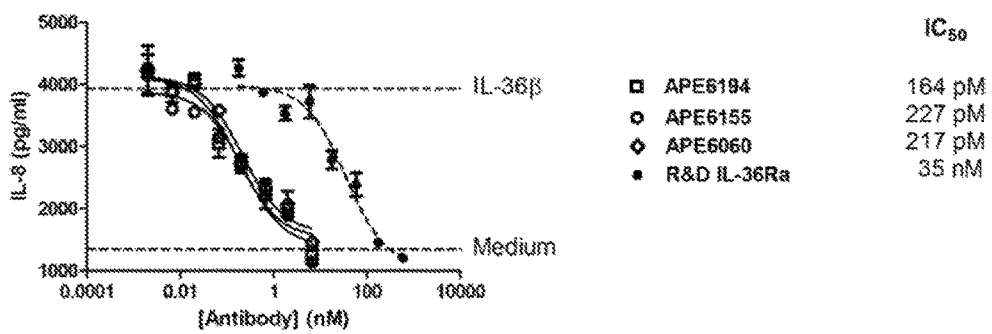
FIG. 4E is a graph depicting the results of the IL-8 secretion assay in primary human keratinocytes described in Example 3 using 1 ng/mL hIL-36β.
Figure 4F:
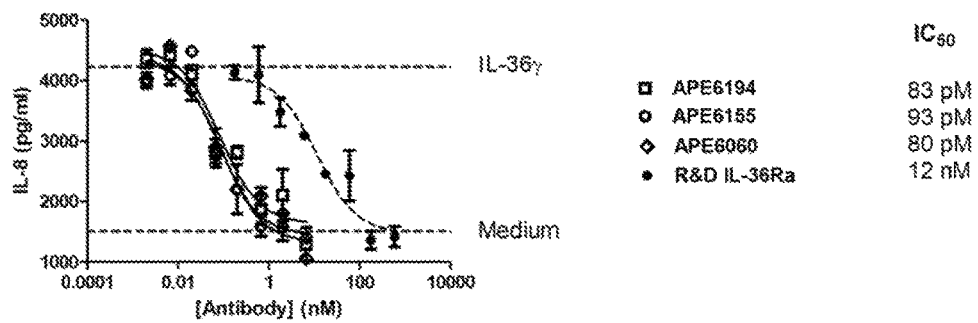
FIG. 4F is a graph depicting the results of the IL-8 secretion assay in primary human keratinocytes described in Example 3 using 100 ng/mL hIL-36γ.
Figure 4G:
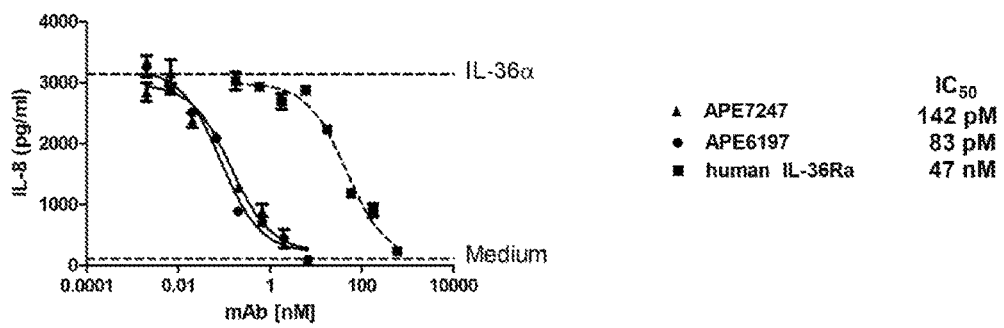
FIG. 4G is a graph depicting the results of the IL-8 secretion assay in primary human keratinocytes described in Example 3 using 10 ng/mL hIL-36α.
Figure 4H:
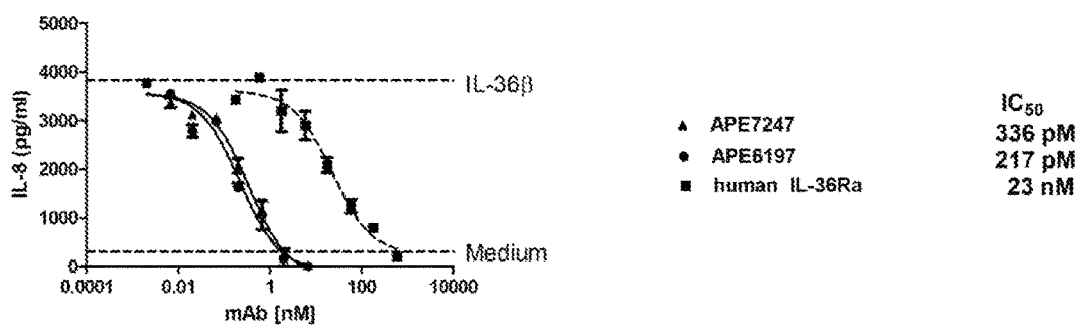
FIG. 4H is a graph depicting the results of the IL-8 secretion assay in primary human keratinocytes described in Example 3 using 1 ng/mL hIL-36β.
Figure 4I:
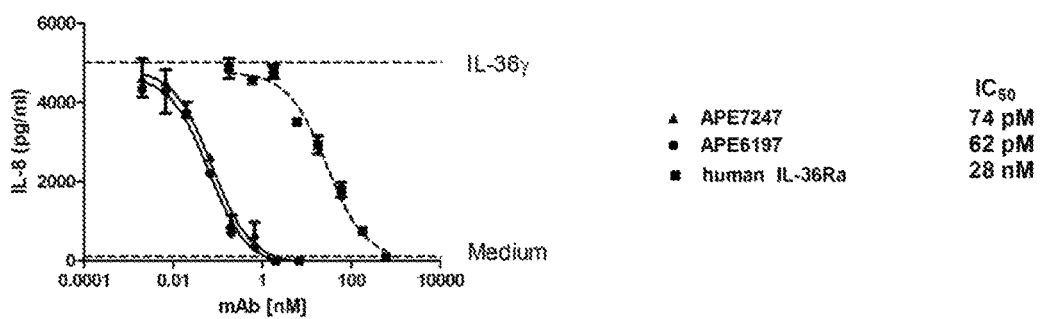
FIG. 4I is a graph depicting the results of the IL-8 secretion assay in primary human keratinocytes described in Example 3 using 100 ng/mL hIL-36γ.
Figure 5A:
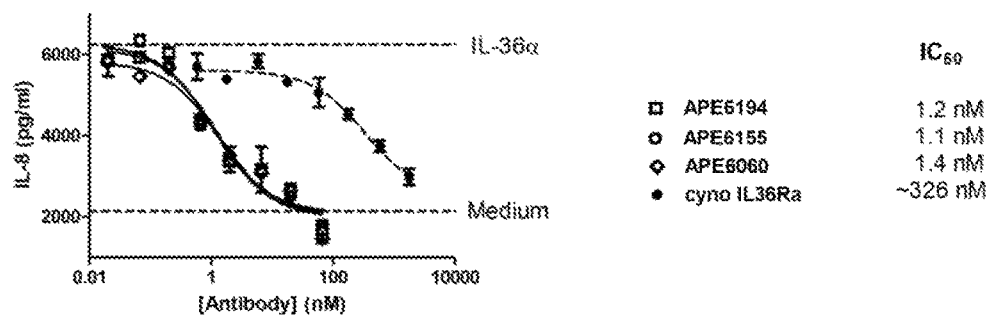
FIG. 5A is a graph depicting the results of the IL-8 secretion assay in primary cynomolgus keratinocytes described in Example 4 using 50 ng/mL cyno IL-36α.
Figure 5B:
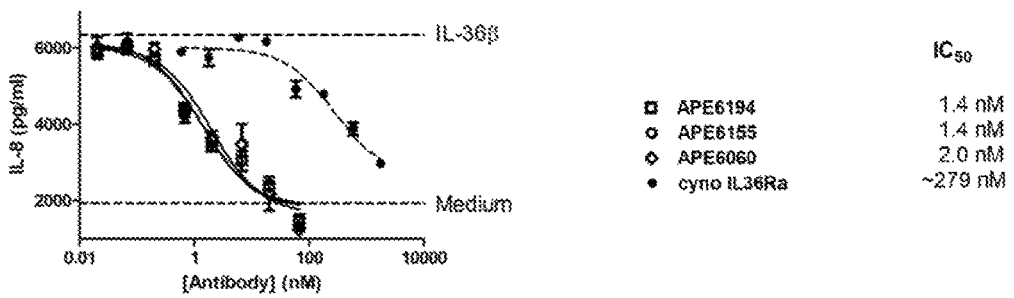
FIG. 5B is a graph depicting the results of the IL-8 secretion assay in primary cynomolgus keratinocytes described in Example 4 using 10 ng/mL cyno IL-36β.
Figure 5C:
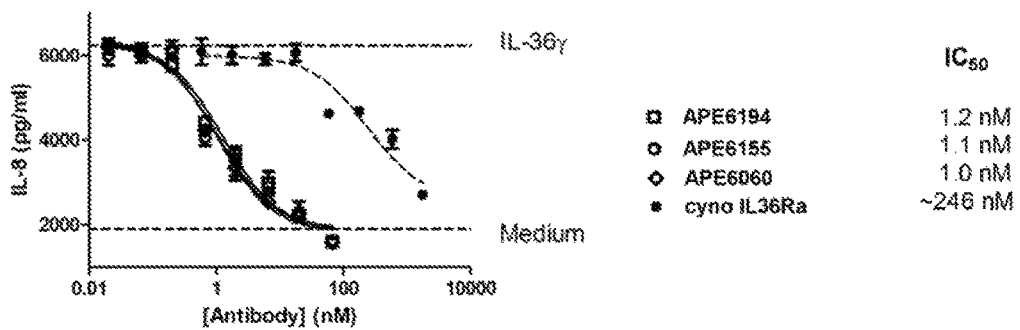
FIG. 5C is a graph depicting the results of the IL-8 secretion assay in primary cynomolgus keratinocytes described in Example 4 using 250 ng/mL cyno IL-36γ.
Figure 5D:
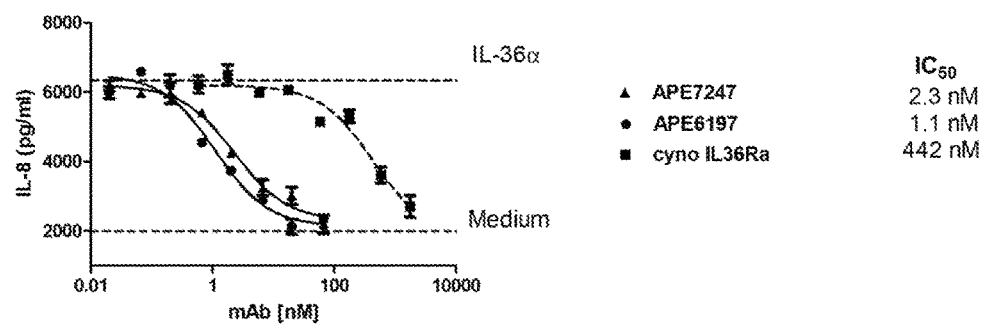
FIG. 5D is a graph depicting the results of the IL-8 secretion assay in primary cynomolgus keratinocytes described in Example 4 using 50 ng/mL cyno IL-36α.
Figure 5E:
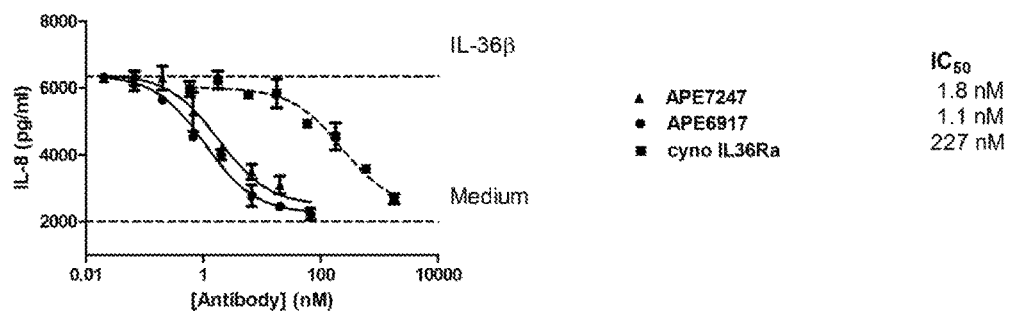
FIG. 5E is a graph depicting the results of the IL-8 secretion assay in primary cynomolgus keratinocytes described in Example 4 using 10 ng/mL cyno IL-36β.
Figure 5F:
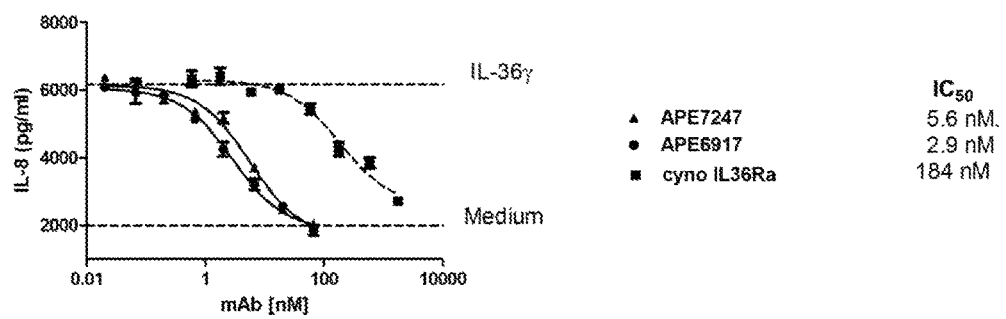
FIG. 5F is a graph depicting the results of the IL-8 secretion assay in primary cynomolgus keratinocytes described in Example 4 using 250 ng/mL cyno IL-36γ.

The resulting KD values of the BIACORE™ T200 and KINEXA® 3000 assays assay are set forth in Table 4 and FIG. 3A (KinExA data for Humanized 1D9), FIG. 3B (Biacore for 5D3 APE6194) and FIG. 3C (KinExA data for Humanized 18D4).

TABLE 4

| Description | Antibody | BIACORE™ KD human IL-36R | BIACORE™ KD cyno IL-36R | KINEXA™ KD human IL-36R |
|---|---|---|---|---|
| 1D9 Humanized | APE5281 | 77 pM | 126 pM | 8 pM |
| 5D3 Chimeric | APE3850 | 35 pM | | |
| 5D3 Humanized | APE6060 | 50 pM | | |
| 5D3 Humanized | APE6155 | 71 pM | | 169 pM |
| 5D3 Humanized | APE6194 | 22 pM | | |
| 18D4 Humanized | APE7247 | <20 pM | <20 pM | 100 pM |
| 18D4 Humanized | APE6904 | | | 27 pM |

These data demonstrate that antibodies comprising different combinations of the inventive immunoglobulin HC and LC polypeptides described herein can bind human IL-36R with high affinities.

EXAMPLE 3

This example demonstrates that the inventive immunoglobulin heavy chain (HC) and light chain (LC) polypeptides can form antibodies that bind to human IL-36R in vitro and inhibit cell signaling and cytokine (e.g., IL-8) release by human primary keratinocyte cells endogenously expressing IL-36R.

Antibodies used in this assay were produced and purified as described above. Normal human epidermal kerotinocytes (NHEK) were purchased from Lonza Clonetics (cat

00192627). Cells were cultured and expanded using recommended culture medium (Lonza KBM Gold medium, cat #00192151 with Lonza KGM Gold SingleQuot supplements, cat #0092152) in a 5% $CO_2$ 37° C. incubator. Cells were frozen in liquid nitrogen at passage 2 in multiple single use aliquots.

Passage 2 cells were thawed and diluted to a density of 100,000 cells per ml in above recommended culture medium described above and 100 µl cells per well were plated in standard flat-bottom 96-well tissue culture plates for a final cell density of 10,000 cells per well. Outside wells are filled with 200 µl phosphate buffered saline per well to avoid edge effects. Cells were cultured overnight in a 5% $CO_2$ 37° C. incubator to allow for adherence.

The following day antibodies were added at concentrations from 10 µg/ml or 1 µg/ml down to 0 by half-log dilutions in culture medium. After 30 minutes, recombinant human IL-36 ligands were added at approximately $EC_{50}$ concentrations (previously determined empirically for each ligand) in culture medium. Antibody and ligand concentrations were made at 4× of desired final concentrations and 50 µl per well were added for a final total volume in each well of 200 µl. Supernatants were removed approximately 48 hours later following a three-minute centrifugation of the plates, transferred to clean plates, and either tested immediately or stored at −80° C. until further analysis.

Human IL-8 levels in the cell supernatants were assessed by ELISA using R&D Systems DUO-SET™ ELISA kit (cat #DY208) following a standard protocol provided by the manufacturer. Data were graphed and $IC_{50}$ values were calculated using GraphPad PRISM™ software.

The results of this assay are shown in Table 5 and FIGS. 4A-4I.

tides can form antibodies that bind to cynomolgus IL-36R (cyno IL-36R) in vitro and inhibit IL-36-dependent cell signaling and cytokine (e.g., IL-8) release by primary keratinocyte cells endogenously expressing IL-36R.

Antibodies used in this assay were produced and purified as described in Example 3. Normal cynomolgus monkey epidermal kerotinocytes were purchased from CellBiologics (Chicago, Ill.; cat #MK-6066K). Cells were cultured and expanded using recommended culture medium (CellBiologics epithelial medium, cat #M6621 with CellBiologics epithelial cell medium supplements, cat #M6621-kit) in a 5% $CO_2$ 37° C. incubator. Cells were frozen in liquid nitrogen at passage 2 in multiple single use aliquots.

Passage 2 cells were thawed and diluted to a density of 100,000 cells per ml in culture medium described above, and 100 µl cells per well were plated in standard flat-bottom 96-well tissue culture plates for final a cell density of 10,000 cells per well. Outside wells were filled with 200 µl PBS per well to avoid edge effects. Cells were cultured overnight in a 5% $CO_2$ 37° C. incubator to allow for adherence.

The following day antibodies were added at concentrations from 10 µg/ml or 1 µg/ml down to 0 by half-log dilutions in culture medium. After 30 minutes, recombinant cynomolgus IL-36 ligands were added at approximately $EC_{50}$ concentrations (previously determined empirically for each ligand) in culture medium. Antibody and ligand concentrations were made at 4× of desired final concentrations and 50 µl per well were added for a final total volume in each well of 200 µl. Supernatants were removed approximately 48 hours later following a three-minute centrifugation of the

TABLE 5

| Antibody | HC SEQ ID NO: | LC SEQ ID NO: | EC50 (nM) 10 ng/ml human IL-36α | EC50 (nM) 1 ng/ml human IL-36β | EC50 (nM) 100 ng/ml human IL-36γ |
|---|---|---|---|---|---|
| Humanized (HzD) 1D9 (APE5281) | 6 | 39 | 0.047 | 0.053 | 0.04 |
| Hzd 5D3 (APE6060) | 22 | 43 | 0.08 | 0.217 | 0.08 |
| Hzd 5D3 (APE6155) | 22 | 44 | 0.125 | 0.227 | 0.093 |
| Hzd 5D3 (APE6194) | 24 | 44 | 0.105 | 0.164 | 0.083 |
| Hzd 18D4 (APE7247) | 52 | 55 | 0.142 | 0.336 | 0.074 |

The results of this example demonstrate that antibodies composed of combinations of HCs and LCs described herein inhibit inflammatory cytokine release (IL-8) from human primary keratinocytes expressing IL-36R and stimulated with cytokines IL-36α, IL-36β and IL-36γ in a dose-dependent manner.

EXAMPLE 4

This example demonstrates that the inventive immunoglobulin heavy chain (HC) and light chain (LC) polypepplates, transferred to clean plates, and either tested immediately or stored at −80° C. until further analysis.

Cynomolgus IL-8 levels in the cell supernatants were assessed by ELISA using a eBioscience (San Diego, Calif.) monkey IL-8 platinum ELISA kit (cat #BMS640/3) following a standard protocol provided by the manufacturer. Data were graphed and $IC_{50}$ values were calculated using GraphPad PRISM™ software.

The results of this assay are shown in Table 6 and FIGS. 5A-5F.

TABLE 6

| Antibody | HC SEQ ID NO: | LC SEQ ID NO: | EC50 (nM) 50 ng/ml cyno IL-36α | EC50 (nM) 10 ng/ml cyno IL-36β | EC50 (nM) 250 ng/ml cyno IL-36γ |
|---|---|---|---|---|---|
| Hzd 5D3 (APE6060) | 22 | 43 | 1.4 | 1.4 | 1.0 |
| Hzd 5D3 (APE6155) | 22 | 44 | 1.1 | 1.4 | 1.1 |
| Hzd 5D3 (APE6194) | 24 | 44 | 1.2 | 2.0 | 1.2 |
| Hzd 18D4 (APE7247) | 52 | 55 | 2.3 | 1.8 | 5.6 |

The results of this example demonstrate that antibodies composed of combinations of HCs and LCs described herein inhibit inflammatory cytokine release (IL-8) from cynomolgus primary keratinocytes expressing IL-36R and stimulated with cytokines IL-36α, IL-36β and IL-36γ in a dose-dependent manner.

EXAMPLE 5

This example demonstrates the ability of antibodies composed of HCs and LCs described herein to block, in a dose-dependent manner, the human IL-36-mediated release of IL-8 from human monocytes expressing the IL-36R.

A Leukocyte Reduction System unit processed from a donor whole blood unit was obtained from the San Diego Blood Bank. Peripheral blood mononuclear cells (PBMCs) were prepped by standard methods using Ficoll density centrifugation separation (Sigma HISTOPAQUE™ cat #10771). Monocytes were isolated from PBMCs with human monocyte isolation kit II (Miltenyi Biotec, San Diego, Calif.; cat #130-091-153).

Monocytes were diluted to a density of 500,000 cells/ml in RPMI 1640 medium containing 10% fetal bovine serum and penicillin/streptomycin, and 100 μl cells per well were plated in standard flat-bottom 96-well tissue culture plates for a final cell density of 50,000 per well. Outside wells were filled with 200 μl PBS per well to avoid edge effects. Plated cells were incubated for 2-3 hours in a 5% $CO_2$ 37° C. incubator to allow for recovery.

After approximately 2-3 hours of culture, antibodies were added at concentrations from 10 μg/ml or 1 μg/ml down to 0 by half-log dilutions in culture medium. After 30 minutes, recombinant human IL-36 ligands were added at approximately $EC_{50}$ concentrations (previously determined empirically for each ligand) in culture medium. Antibody and ligand concentrations were made at 4× of desired final concentrations and 50 μl per well were added for a final total volume in each well of 200 μl. Supernatants were removed approximately 48 hours later following a three-minute centrifugation of the plates, transferred to clean plates, and either tested immediately or stored at −80° C. until further analysis.

Human IL-8 levels in the cell supernatants were assessed by ELISA using R&D Systems DUO-SET™ ELISA kit (cat #DY208) following a standard protocol provided by the manufacturer. Data were graphed and $IC_{50}$ values were calculated using GraphPad PRISM™ software.

Figure 6A:
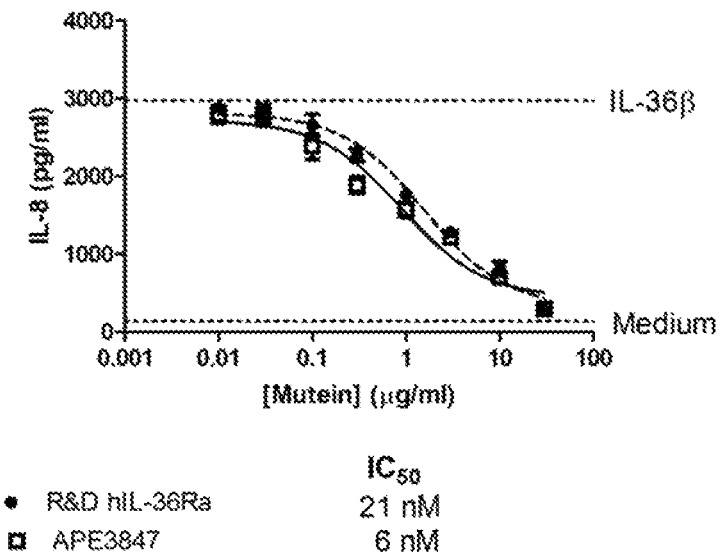
FIG. 6A is a graph depicting the results of the IL-8 secretion assay in primary human monocytes described in Example 5 using 5 ng/mL of IL-36β.
Figure 6B:
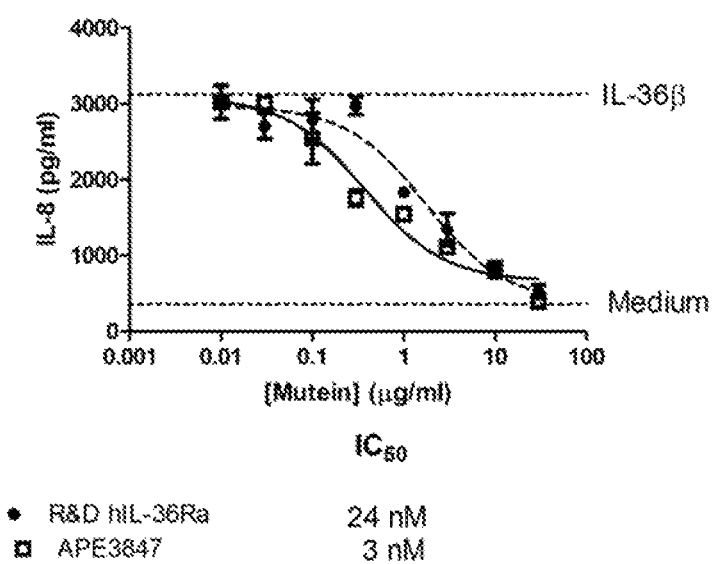
FIG. 6B is a graph depicting the results of the IL-8 secretion assay in primary human monocytes described in Example 5 using 500 ng/mL IL-36β.

The results of these experiments are set forth in Table 7 and FIGS. 6A and 6B.

TABLE 7

| Antibody | HC SEQ ID NO: | LC SEQ ID NO: | EC50 (nM) human IL-36α | EC50 (nM) human IL-36β | EC50 (nM) human IL-36γ |
|---|---|---|---|---|---|
| Chimeric 1D9 (APE3798) | 33 | 48 | | | |
| HzD 1D9 (APE5281) | 6 | 39 | 0.035 | 0.033 | 0.027 |
| Chimeric 5D3 (APE3849) | 34 | 49 | | | |
| Hzd 5D3 (APE6060) | 22 | 43 | 0.081 | 0.90 | 0.79 |
| Hzd 5D3 (APE6155) | 22 | 44 | 0.088 | 0.117 | 0.078 |
| Hzd 5D3 (APE6194) | 24 | 44 | 0.09 | 0.105 | 0.084 |
| Chimeric 18D4 (APE3847) | 35 | 50 | | 6.0 | 3.0 |

The results of this example demonstrate that antibodies composed of combinations of HCs and LCs described herein inhibit inflammatory cytokine release (IL-8) from human primary monocytes expressing IL-36R and stimulated with cytokines IL-36α, IL-36β and IL-36γ in a dose-dependent manner.

EXAMPLE 6

This example demonstrates that the inventive immunoglobulin heavy chain (HC) and light chain (LC) polypeptides described herein can form antibodies that inhibit IL-36-dependent cytokine release from human primary peripheral blood mononuclear cells.

A Leukocyte Reduction System unit processed from a donor whole blood unit was obtained from the San Diego Blood Bank. Peripheral blood mononuclear cells (PBMCs) were prepped by standard methods using Ficoll density centrifugation separation (Sigma HIS TOPAQUE™ cat #10771).

PBMCs were diluted to density of 1×10⁶ cells/ml in RPMI 1640 medium containing 10% fetal bovine serum and penicillin/streptomycin, and 100 µl cells per well were plated in standard flat-bottom 96-well tissue culture plates for a final cell density of 100,000 per well. Outside wells were filled with 200 µl PBS per well to avoid edge effects. Plated cells were incubated for 2-3 hours in a 5% $CO_2$ 37° C. incubator to allow for recovery.

After approximately 2-3 hours of culture, antibodies were added at concentrations from 10 µg/ml or 1 µg/ml down to 0 by half-log dilutions in culture medium. After 30 minutes, recombinant human IL-36 ligands were added at approximately $EC_{50}$ concentrations (previously determined empirically for each ligand) in culture medium. Antibody and ligand concentrations were made at 4× of desired final concentrations and 50 µl per well were added for a final total volume in each well of 200 µl. Supernatants were removed approximately 48 hours later following a three-minute centrifugation of the plates, transferred to clean plates, and either tested immediately or stored at −80° C. until further analysis.

Human IL-8 levels in the cell supernatants were assessed by ELISA using R&D Systems DUO-SET™ ELISA kit (cat #DY208) following a standard protocol provided by the manufacturer. Data were graphed and $IC_{50}$ values were calculated using GraphPad PRISM™ software.

Figure 7A:
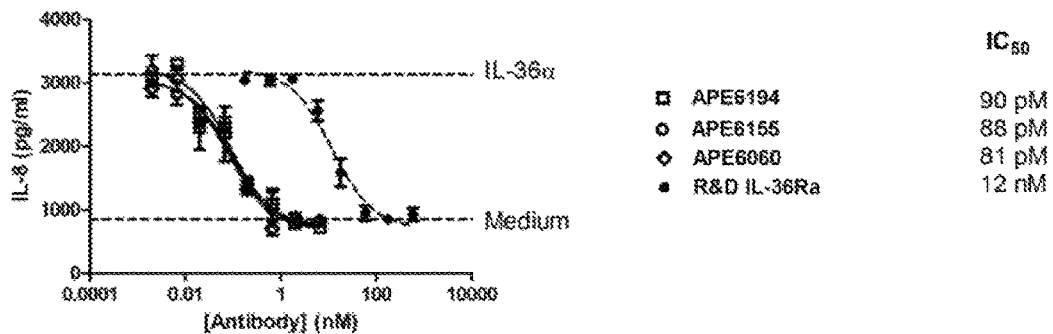
FIG. 7A is a graph depicting the results of the IL-8 secretion assay in primary human peripheral blood mononuclear cells (PBMCs) described in Example 6 using 10 ng/mL of IL-36α.
Figure 7B:
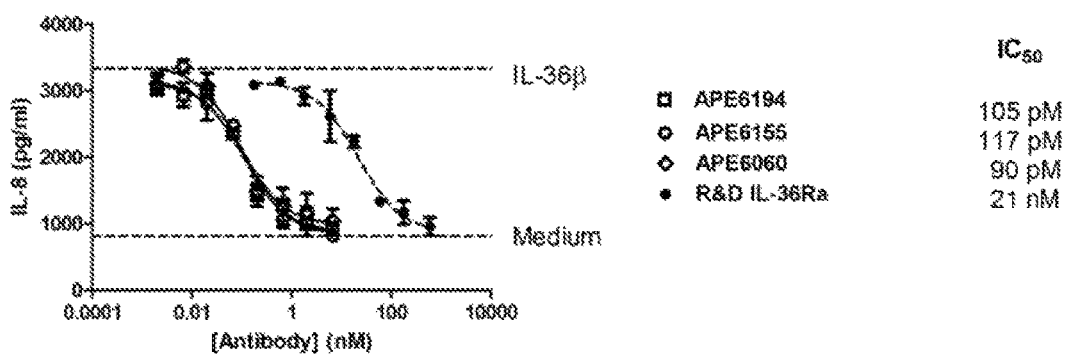
FIG. 7B is a graph depicting the results of the IL-8 secretion assay in primary human peripheral blood mononuclear cells (PBMCs) described in Example 6 using 1 ng/mL IL-36β.
Figure 7C:
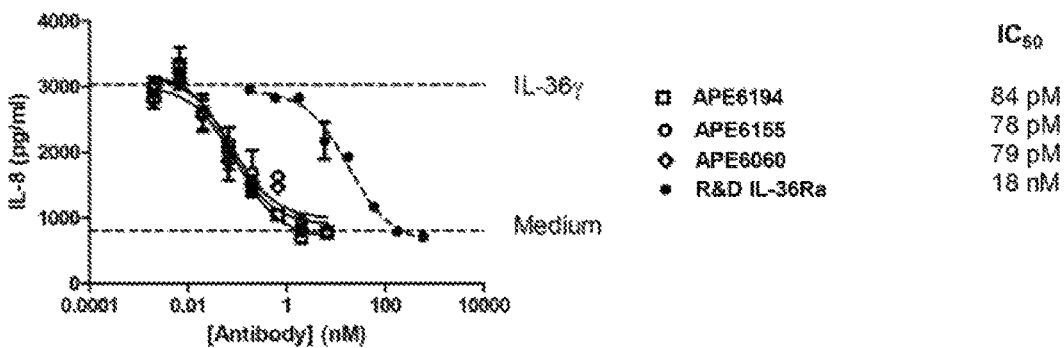
FIG. 7C is a graph depicting the results of the IL-8 secretion assay in primary human peripheral blood mononuclear cells (PBMCs) described in Example 6 using 100 ng/mL IL-36γ.

The results of this assay are shown in FIGS. 7A-7C, and demonstrate that antibodies composed of combinations of HCs and LCs described herein inhibit inflammatory cytokine release (IL-8) from human primary peripheral blood mononuclear cells expressing IL-36R and stimulated with cytokines IL-36α, IL-36β and IL-36γ in a dose-dependent manner.

EXAMPLE 7

This example demonstrates that the inventive immunoglobulin heavy chain (HC) and light chain (LC) polypeptides described herein can form antibodies that inhibit IL-36-dependent cytokine release from cynomolgus primary peripheral blood mononuclear cells.

Peripheral blood mononuclear cells (PBMCs) were prepped by standard methods using Ficoll density centrifugation separation (Sigma HISTOPAQUE™; cat #10771) from normal cynomolgus monkey whole blood obtained from Biotox Sciences (San Diego, Calif.).

PBMCs were diluted to a density of 1×10⁶ cells/ml in RPMI 1640 medium containing 10% fetal bovine serum and penicillin/streptomycin, and 100 µl cells per well were plated in standard flat-bottom 96-well tissue culture plates for a final cell density of 100,000 per well. Outside wells are filled with 200 µl PBS per well to avoid edge effects. Plated cells were incubated for 2-3 hours in a 5% $CO_2$ 37° C. incubator to allow for recovery.

After approximately 2-3 hours of culture, antibodies were added at concentrations from 10 µg/ml or 1 µg/ml down to 0 by half-log dilutions in culture medium. After 30 minutes, recombinant cynomolgus IL-36 ligands were added at approximately $EC_{50}$ concentrations (previously determined empirically for each ligand) in culture medium. Antibody and ligand concentrations were made at 4× of desired final concentrations and 50 µl per well were added for a final total volume in each well of 200 µl. Supernatants were removed approximately 48 hours later following a three-minute centrifugation of the plates, transferred to clean plates, and either tested immediately or stored at −80° C. until further analysis.

Cynomolgus IL-8 levels in the cell supernatants were assessed by ELISA using eBioscience monkey IL-8 platinum ELISA kit (San Diego, Calif.; cat #BMS640/3) following a standard protocol provided by the manufacturer. Data were graphed and $IC_{50}$ values were calculated using GraphPad PRISM™ software. The results of this assay are set forth in Table 8.

TABLE 8

| Antibody | HC SEQ ID NO: | LC SEQ ID NO: | EC50 (nM) 50 ng/ml cyno IL-36α | EC50 (nM) 10 ng/ml cyno IL-36β | EC50 (nM) 250 ng/ml cyno IL-36γ |
|---|---|---|---|---|---|
| Hzd 5D3 (APE6060) | 22 | 43 | 0.98 | 1.7 | 1.4 |
| Hzd 5D3 (APE6155) | 22 | 44 | 1.2 | 1.5 | 0.89 |
| Hzd 5D3 (APE6194) | 24 | 44 | 1.5 | 1.6 | 1.6 |

The results of this example demonstrate that antibodies composed of combinations of HCs and LCs described herein inhibit inflammatory cytokine release (IL-8) from cynomolgus primary peripheral blood mononuclear cells expressing IL-36R and stimulated with cytokines IL-36α, IL-36β and IL-36γ in a dose-dependent manner.

EXAMPLE 8

This example demonstrates that the inventive immunoglobulin heavy chain (HC) and light chain (LC) polypeptides described herein can form antibodies that cross-compete for binding to human IL-36R.

Cross-competition binding of the target IL-36R by antibodies comprising various HC and LC polypeptides described herein was determined using a BIACORE™ T200 system (GE Healthcare, Little Chalfont, Buckinghamshire, UK). In each assay, the primary antibody was captured on the surface of the chip, and unutilized capture sites were subsequently blocked by addition of saturating amounts of a negative control antibody which does not bind human IL-36R. This step was followed by binding of IL-36R and subsequent addition of the secondary antibody to determine if the antibodies were competing for the same binding site on the monomeric antigen. If antibodies bind the same epitope, no secondary binding would be observed; if different binding sites on the IL-36R are utilized, the secondary antibody would bind to the primary antibody/antigen complex.

Anti-human IgG (Fc-specific; GE Healthcare, Chalfont St. Giles, United Kingdom) was immobilized on the surface of a BIACORE™CM5 chip at ~8,000 RU using EDC-activated coupling chemistry. Anti-IL-36R antibodies comprising various combinations of the inventive HC and LC polypeptides described herein (10 µg/mL; 60s contact time at a flow rate of 10 µL/min) were then captured on the surface of the chip at 25° C. yielding ~500RU captured antibody. The surface was blocked using a non-specific, isotype-matched negative control antibody to the target (APE4909 at 100 µg/mL; 60 second contact time at a flow rate of 10 µL/min). Subsequently, IL-36R (at 1 µM) diluted in running buffer (HBS-EP+, pH 7.6; GE Healthcare, Chalfont St. Giles, United Kingdom) was run over the surface of the chip (300 seconds at a flow rate of 30 µL/min), and was immediately followed by a secondary antibody. The resulting sensograms generated via surface plasmon resonance (SPR) indirectly monitoring mass changes on the surface of the chip were examined to determine cross competition between the antibodies.

Figure 8A:
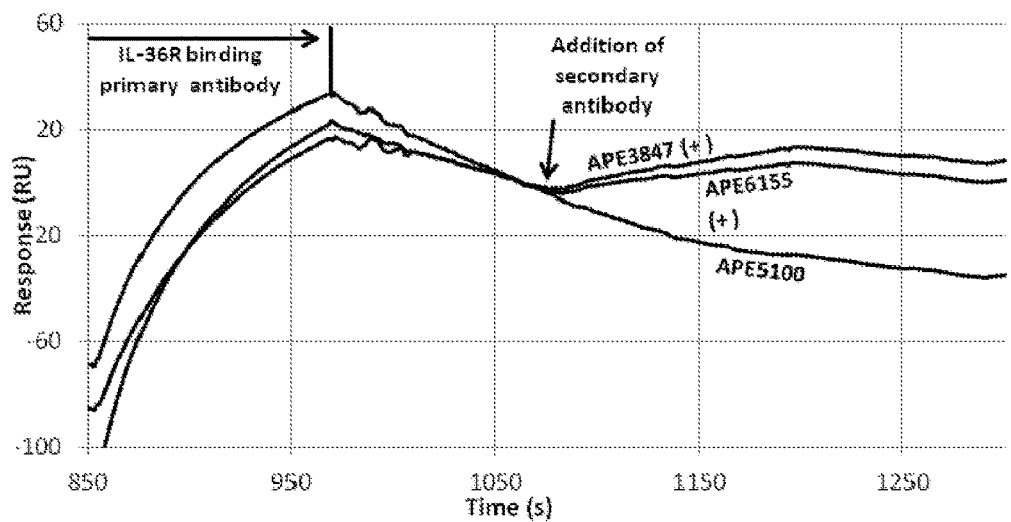
FIG. 8A is a graph depicting the results of the antibody/antigen cross-competition binding assay described in Example 8 as determined by BIACORE™ assay using APE5100 as primary antibody.
Figure 8B:
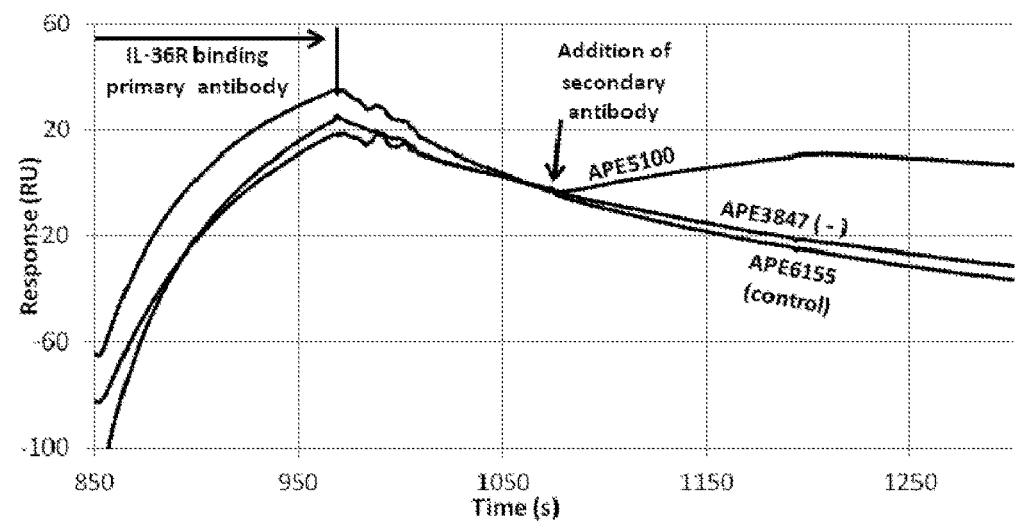
FIG. 8B is a graph depicting the results of the antibody/antigen cross-competition binding assay described in Example 8 as determined by BIACORE™ assay using APE6155 as primary antibody.

The results of the competitive binding assays for the inventive anti-IL-36R antibodies are shown in Table 9 and FIGS. 8A and 8B.

TABLE 9

| Primary Antibody | HC SEQ ID NO: | LC SEQ ID NO: | Secondary Antibodies | | |
|---|---|---|---|---|---|
| | | | APE3847 (18D4) | APE5100 (1D9) | APE6155 (5D3) |
| APE3847 (18D4) | 35 | 50 | Competition | No competition | Competition |
| APE5100 (1D9) | 4 | 39 | No competition | Competition | No competition |
| APE6155 (5D3) | 22 | 44 | Competition | No competition | Competition |

The results of this example demonstrate that the antibodies APE6155 (5D3) and APE3847 (18D4) compete for binding to the same epitope on human IL-36R, but do not compete with the antibody APE5100 for binding to IL-36R, suggesting that neither APE6155 nor APE3847 shares an epitope with APE5100. Competition results were consistent and independent of the ordering of the primary and secondary antibody binding to antigen.

EXAMPLE 9

This example demonstrates that the inventive immunoglobulin heavy chain (HC) and light chain (LC) polypeptides described herein can bind to cells expressing the human and cynomolgus monkey IL-36R with IL-1RAcP.

The binding of antibodies to CHO-K cells stably co-expressing human IL-36R and human IL-1RAcP was examined. Cynomolgus IL-36R allelic variation was examined by Sanger sequencing, and four distinct allelic variants were identified within cynomolgus monkey populations. The binding of antibodies to CHO-K cells stably co-expressing cynomolgus monkey IL-36R variant 1 and cynomolgus monkey IL-1RAcP was also examined for APE6155 and APE7247. Each antibody was incubated with CHO cells harvested using accutase, washed, and seeded at 500,000 cells per well. Cells were incubated with antibodies at concentrations ranging from 33nM-16 pM for 30 minutes at 4° C., and washed three times with FACS staining buffer. Cells were spun and aspirated, and then the incubated with 100 µl paraformaldehyde for 10 minutes at room temperature. Cells were again washed, aspirated, and stained with 100 µL of anti-human IgG Alexa 647 for 20 minutes at 4° C. Cells were resuspended in 100 µL FACS analysis buffer before analysis on the FACS Array (BD Biosciences).

Figure 9A:
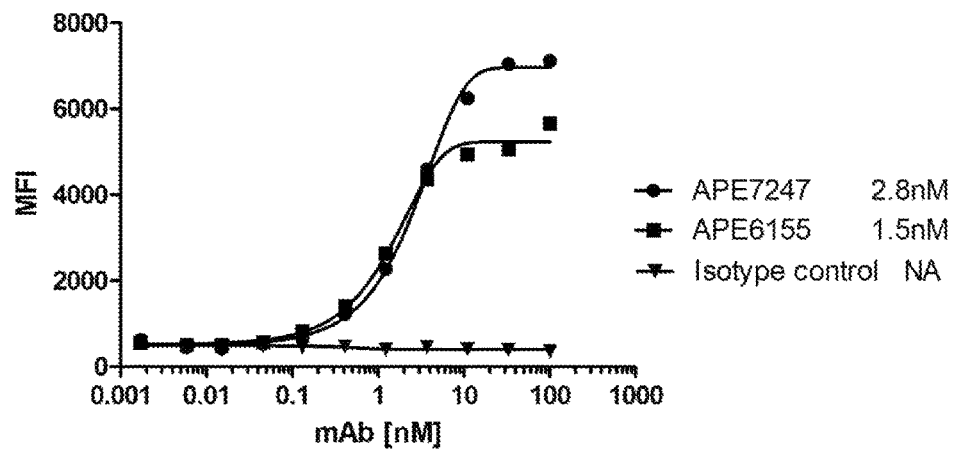
FIG. 9A is a graph depicting the results of the competitive binding assay described in Example 9 using CHO-K cells stably co-expressing human IL-36R and human IL-1RAcP.
Figure 9B:
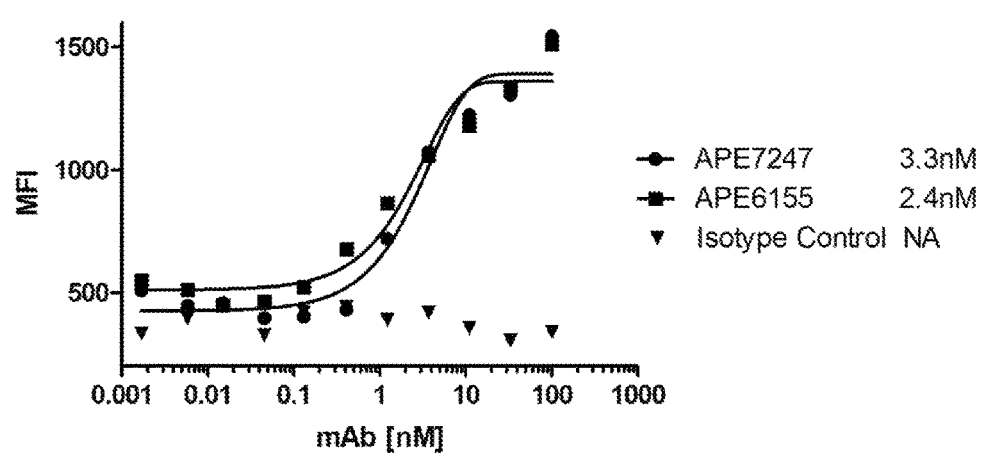
FIG. 9B is a graph depicting the results of the competitive binding assay described in Example 9 using CHO-K cells stably co-expressing cynomolgus monkey IL-36R variant 1 and cynomolgus monkey IL-1RAcP.

The results of the competitive binding assays for the inventive anti-IL-36R antibodies are shown in FIGS. 9A and 9B. FIG. 9A shows binding of APE06155 and APE07247 antibodies to CHO cells stably expressing human IL-36R and human IL-36R, and FIG. 9B shows the same antibodies binding to CHO cells stably expressing cynomolgus monkey variant 1 IL-36R and IL-1RAcP. Data were fit using Graphpad Prism software, with EC50 values for APE6155 determined as 1.5 nM and 2.4 nM to human and cynomolgus IL-36R expressing CHO cells respectively, and 2.8 nM and 3.3 nM for backup Ab APE7247 binding to human and cynomolgus IL-36R expressing CHO cells, respectively. The negative isotype matched control antibody APE00422 showed no binding to either cell line.

EXAMPLE 10

This example demonstrates that the inventive immunoglobulin heavy chain (HC) and light chain (LC) polypeptides described herein can be used in vivo in Cynomologous monkey with good pharmacokinetic characteristics and subcutaneous bioavailability. Cynomologous monkeys were dosed with ANB019 as a single dose intravenous (IV) or subcutaneous (SC) injection. Blood samples were collected from the monkeys in the single dose study from 0.5 to 672 hrs (4 wks) after dosing. The derived serum samples were analyzed at AnaptysBio, Inc. (San Diego, Calif.) using an in-house ELISA-based method. Pharmacokinetic analyses were performed on the serum concentration of ANA020 versus time data by AnaptysBio, Inc.

Serum concentration vs. time profiles of ANB019 behaved normally for both dose routes, IV and SC, with levels dropping rapidly from Tmax through the 24 hr time point for the IV administration, followed by a decline in line with the expected behavior of a monoclonal antibody in a nonhuman primate. Pharmacokinetic parameter estimates from the ANB019 serum concentration values were derived from a non-compartmental analysis and are listed in Table 10. Parameter estimates were consistent with the anticipated pharmacokinetics for an IgG4 scaffold monoclonal antibody in the monkey. The half-life of ANB019 was estimated to be ~270 hrs after IV injection and ~330 hrs after SC injection. Bioavailability after SC injection was 60%.

TABLE 10

| | IgG4 IV | IgG4 SC |
|---|---|---|
| $AUC_{0-672\ hrs}$ (hr*ng/mL) | 70,834,325 | 42,680,650 |
| $T_{1/2}$ (hrs) | 271 | 331 |
| $C_{max}$ (ng/mL) | 757,588 | 149,518 |
| $T_{max}$ (hrs) | 0.5 | 28 |
| Bioavailability (%) | | 60 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An interleukin-36 receptor (IL-36R) binding agent comprising an immunoglobulin heavy chain comprising CDR1, CDR2, and CDR3 of SEQ ID NO: 22, and an immunoglobulin light chain comprising CDR1, CDR2, and CDR3 of SEQ ID NO: 44, wherein the IL-36R binding agent is an antibody or antigen-binding antibody fragment.

2. The IL-36R binding agent of claim 1, wherein the IL-36R binding agent is part of an antibody conjugate.

3. The IL-36R-binding agent of claim 1, wherein the IL-36R binding agent is a F(ab')$_2$, Fab', Fab, Fv, scFv, dsFv, or a single chain binding polypeptide.

4. The IL-36R-binding agent of claim 1, wherein the IL-36R binding agent is an IgG1 antibody.

5. The IL-36R binding agent of claim 1, wherein the IL-36R-binding agent binds to IL-36R with a $K_D$ between about 1 picomolar (pM) and about 200 pM when measured by surface plasmon resonance analysis.

6. A pharmaceutical composition comprising (a) the IL-36R-binding agent of claim 1, and (b) a pharmaceutically acceptable carrier.

7. An anti-interleukin-36 receptor (IL-36R) binding agent comprising the immunoglobulin heavy chain variable region of SEQ ID NO: 22, and the immunoglobulin light chain variable region of SEQ ID NO: 44, wherein the IL-36R binding agent is an antibody or antigen-binding antibody fragment.

8. The IL-36R binding agent of claim 7, wherein the IL-36R binding agent is part of an antibody conjugate.

9. The IL-36R-binding agent of claim 7, wherein the IL-36R binding agent is a F(ab')$_2$, Fab', Fab, Fv, scFv, dsFv, or a single chain binding polypeptide.

10. The IL-36R-binding agent of claim 7, wherein the IL-36R binding agent is an IgG1 antibody.

11. The IL-36R binding agent of claim 7, wherein the IL-36R-binding agent binds to IL-36R with a $K_D$ between about 1 picomolar (pM) and about 200 pM when measured by surface plasmon resonance analysis.

12. A pharmaceutical composition comprising (a) the IL-36R-binding agent of claim 7, and (b) a pharmaceutically acceptable carrier.

13. A method of treating a disorder in a mammal that is responsive to IL-36R inhibition, which method comprises administering an effective amount of the IL-6R binding agent of claim 1 to a mammal with a disorder that is responsive to IL-36R inhibition, whereupon the disorder is treated.

14. The method of claim 13, wherein the IL-36R binding agent is part of an antibody conjugate.

15. The method of claim 13, wherein the IL-36R binding agent is a F(ab')$_2$, Fab', Fab, Fv, scFv, dsFv, dAb, or a single chain binding polypeptide.

16. The method of claim 13, wherein the half-life of the IL-36R-binding agent in the mammal is between 30 minutes and 45 days.

17. The method of claim 13, wherein the IL-36R-binding agent binds to IL-36R with a $K_D$ between about 1 picomolar (pM) and about 200 pM when measured by surface plasmon resonance analysis.

18. A method of treating a disorder in a mammal that is responsive to IL-36R inhibition, which method comprises administering an effective amount of the IL-36R binding agent of claim 7 to a mammal with a disorder that is responsive to IL-36R inhibition, whereupon the disorder is treated.

19. The method of claim 18, wherein the IL-36R binding agent is part of an antibody conjugate.

20. The method of claim 18, wherein the IL-36R binding agent is a F(ab')$_2$, Fab', Fab, Fv, scFv, dsFv, dAb, or a single chain binding polypeptide.

21. The method of claim 18, wherein the half-life of the IL-36R-binding agent in the mammal is between 30 minutes and 45 days.

22. The method of claim 18, wherein the IL-36R-binding agent binds to IL-36R with a $K_D$ between about 1 picomolar (pM) and about 200 pM when measured by surface plasmon resonance analysis.

23. A nucleic acid encoding the immunoglobulin heavy chain and/or immunoglobulin light chain of the IL-36R binding agent of claim 1, optionally in a vector.

24. An isolated cell comprising the nucleic acid of claim 23.

25. A method of preparing an IL-36R binding agent of claim 1, the method comprising expressing in a cell in vitro a nucleic acid sequence encoding the immunoglobulin heavy chain of claim 1, and a nucleic acid sequence encoding the immunoglobulin light chain of claim 1.

26. A nucleic acid encoding the immunoglobulin heavy chain and/or immunoglobulin light chain of IL-36R binding agent of claim 7, optionally in a vector.

27. An isolated cell comprising the nucleic acid of claim 26.

28. A method of preparing an IL-36R binding agent of claim 7, the method comprising expressing in a cell in vitro a nucleic acid sequence encoding the immunoglobulin heavy chain of claim 7, and a nucleic acid sequence encoding the immunoglobulin light chain of claim 7.

* * * * *

UNITED STATES PATENT AND TRADEMARK OFFICE
CERTIFICATE OF CORRECTION

PATENT NO. : 10,526,410 B2
APPLICATION NO. : 15/567045
DATED : January 7, 2020
INVENTOR(S) : Bowers et al.

Page 1 of 1

It is certified that error appears in the above-identified patent and that said Letters Patent is hereby corrected as shown below:

In the Claims

Claim 13, Column 95, Line 44:
Delete "IL-6R" and replace with --IL-36R--.

Signed and Sealed this
Seventh Day of April, 2020

Andrei Iancu
*Director of the United States Patent and Trademark Office*

SEQUENCE LISTING

```
<160> NUMBER OF SEQ ID NOS: 58

<210> SEQ ID NO 1
<211> LENGTH: 116
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: Xaa1 is leucine (Leu) or phenylalanine (Phe)
<220> FEATURE:
<221> NAME/KEY: MISC_FEATURE
<222> LOCATION: (5)..(5)
<223> OTHER INFORMATION: Xaa2 is valine (Val), methionine (Met), or
      leucine (Leu)
<220> FEATURE:
<221> NAME/KEY: MISC_FEATURE
<222> LOCATION: (44)..(44)
<223> OTHER INFORMATION: Xaa3 is arginine (Arg) or glycine (Gly)
<220> FEATURE:
<221> NAME/KEY: MISC_FEATURE
<222> LOCATION: (56)..(56)
<223> OTHER INFORMATION: Xaa4 is glycine (Gly), serine (Ser), or alanine
      (Ala)
<220> FEATURE:
<221> NAME/KEY: MISC_FEATURE
<222> LOCATION: (72)..(72)
<223> OTHER INFORMATION: Xaa5 is arginine (Arg) or alanine (Ala)
<220> FEATURE:
<221> NAME/KEY: MISC_FEATURE
<222> LOCATION: (74)..(74)
<223> OTHER INFORMATION: Xaa6 is threonine (Thr) or lysine (Lys)
<220> FEATURE:
<221> NAME/KEY: MISC_FEATURE
<222> LOCATION: (84)..(84)
<223> OTHER INFORMATION: Xaa7 is serine (Ser) or alanine (Ala)
<220> FEATURE:
<221> NAME/KEY: MISC_FEATURE
<222> LOCATION: (95)..(95)
<223> OTHER INFORMATION: Xaa8 is tyrosine (Tyr) or phenylalanine (Phe)

<400> SEQUENCE: 1

Gln Val Gln Xaa Xaa Gln Ser Gly Ala Glu Val Lys Lys Pro Gly Ala
1               5                   10                  15
```

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Xaa Leu Glu Trp Met
            35                  40                  45

Gly Trp Ile Tyr Pro Gly Asp Xaa Ser Thr Lys Tyr Asn Glu Lys Phe
    50                  55                  60

Lys Gly Arg Val Thr Ile Thr Xaa Asp Xaa Ser Ala Ser Thr Ala Tyr
65                  70                  75                  80

Met Glu Leu Xaa Ser Leu Arg Ser Glu Asp Thr Ala Val Tyr Xaa Cys
                85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Gly Ser Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Gly Leu Glu Trp Met
            35                  40                  45

Gly Trp Ile Tyr Pro Gly Asp Gly Ser Thr Lys Tyr Asn Glu Lys Phe
    50                  55                  60

Lys Gly Arg Val Thr Ile Thr Ala Asp Lys Ser Ala Ser Thr Ala Tyr
65                  70                  75                  80

```
Met Glu Leu Ser Ser Leu Arg Ser Glu Asp Thr Ala Val Tyr Phe Cys
             85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 4

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
             85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 5

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Ala Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
             85                  90                  95

Thr Arg Ser Phe Tyr Thr Met Asp Tyr Trp Gly Gln Gly Thr Thr Val
            100                 105                 110

Thr Val Ser Ser
        115
```

```
<210> SEQ ID NO 6
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 6

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 7

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 8

Gln Val Gln Leu Leu Gln Ser Gly Ala Glu Val Lys Lys Pro Gly Ala
1               5                   10                  15
```

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Ser Ser Thr Lys Tyr Asn Glu Lys Phe
 50                  55                  60

Lys Gly Arg Val Thr Ile Thr Ala Asp Lys Ser Ala Asn Thr Ala Tyr
 65                  70                  75                  80

Met Glu Leu Ala Ser Leu Arg Ser Glu Asp Thr Ala Val Tyr Phe Cys
                 85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 9

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Ala Ser Thr Lys Tyr Asn Glu Lys Phe
 50                  55                  60

Lys Gly Arg Val Thr Ile Thr Arg Asp Lys Ser Ala Asn Thr Ala Tyr
 65                  70                  75                  80

Met Glu Leu Ala Ser Leu Arg Ser Glu Asp Thr Ala Val Tyr Phe Cys
                 85                  90                  95

Thr Arg Ser Phe Tyr Thr Met Asp Tyr Trp Gly Gln Gly Thr Thr Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 10

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
            35                  40                  45

Gly Trp Ile Tyr Pro Gly Asp Ser Ser Thr Lys Tyr Asn Glu Lys Phe
 50                  55                  60

Lys Gly Arg Val Thr Ile Thr Arg Asp Lys Ser Ala Asn Thr Ala Tyr

```
                 65                  70                  75                  80
Met Glu Leu Ala Ser Leu Arg Ser Glu Asp Thr Ala Val Tyr Phe Cys
                 85                  90                  95

Thr Arg Ser Phe Tyr Thr Met Asp Tyr Trp Gly Gln Gly Thr Thr Val
                100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 11

Gln Val Gln Phe Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Asp Ile Asn Trp Val Arg Gln Ala Pro Gly Gln Arg Leu Glu Trp Met
            35                  40                  45

Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
                100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 12

Gln Val Gln Phe Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Asp Ile Asn Trp Val Arg Gln Ala Pro Gly Gln Arg Leu Glu Trp Met
            35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
                100                 105                 110

Thr Val Ser Ser
        115
```

<210> SEQ ID NO 13
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 13

```
Gln Val Gln Phe Val Gln Ser Gly Ala Glu Val Lys Lys Pro Gly Ala
1               5                   10                  15
Ser Val Lys Val Ser Cys Lys Ala Ser Gly Phe Thr Phe Thr Ser Tyr
            20                  25                  30
Asp Ile Asn Trp Val Arg Gln Ala Pro Gly Gln Arg Leu Glu Trp Met
        35                  40                  45
Gly Trp Ile Tyr Pro Gly Asp Ser Ser Thr Lys Tyr Asn Glu Lys Phe
    50                  55                  60
Lys Gly Arg Val Thr Ile Thr Ala Asp Lys Ser Ala Asn Thr Ala Tyr
65                  70                  75                  80
Met Glu Leu Ser Ser Leu Arg Ser Glu Asp Thr Ala Val Tyr Phe Cys
                85                  90                  95
Thr Arg Ser Phe Tyr Thr Met Asp Tyr Trp Gly Gln Gly Thr Thr Val
            100                 105                 110
Thr Val Ser Ser
        115
```

<210> SEQ ID NO 14
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 14

```
Gln Val Gln Leu Leu Gln Ser Gly Ala Glu Val Lys Lys Pro Gly Ala
1               5                   10                  15
Ser Val Lys Val Ser Cys Lys Ala Ser Gly Phe Thr Phe Thr Ser Tyr
            20                  25                  30
Asp Ile Asn Trp Val Arg Gln Ala Pro Gly Gln Arg Leu Glu Trp Met
        35                  40                  45
Gly Trp Ile Tyr Pro Gly Asp Ser Ser Thr Lys Tyr Asn Glu Lys Phe
    50                  55                  60
Lys Gly Arg Val Thr Ile Thr Arg Asp Lys Ser Ala Asn Thr Ala Tyr
65                  70                  75                  80
Met Glu Leu Ser Ser Leu Arg Ser Glu Asp Thr Ala Val Tyr Tyr Cys
                85                  90                  95
Thr Arg Ser Phe Tyr Thr Met Asp Tyr Trp Gly Gln Gly Thr Thr Val
            100                 105                 110
Thr Val Ser Ser
        115
```

<210> SEQ ID NO 15
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (33)..(33)
<223> OTHER INFORMATION: Xaa1 is tryptophan (Trp) or tyrosine (Tyr)

```
<220> FEATURE:
<221> NAME/KEY: MISC_FEATURE
<222> LOCATION: (35)..(35)
<223> OTHER INFORMATION: Xaa2 is histidine (His), asparagine (Asn), or
      tyrosine (Tyr)
<220> FEATURE:
<221> NAME/KEY: MISC_FEATURE
<222> LOCATION: (42)..(42)
<223> OTHER INFORMATION: Xaa3 is glycine (Gly) or arginine (Arg)
<220> FEATURE:
<221> NAME/KEY: MISC_FEATURE
<222> LOCATION: (52)..(52)
<223> OTHER INFORMATION: Xaa4 is aspartic acid (Asp), glutamic acid
      (Glu), or histidine (His)
<220> FEATURE:
<221> NAME/KEY: MISC_FEATURE
<222> LOCATION: (54)..(54)
<223> OTHER INFORMATION: Xaa5 is serine (Ser), threonine (Thr), or
      tyrosine (Tyr)
<220> FEATURE:
<221> NAME/KEY: MISC_FEATURE
<222> LOCATION: (55)..(55)
<223> OTHER INFORMATION: Xaa6 is asparagine (Asn) or glycine (Gly)
<220> FEATURE:
<221> NAME/KEY: MISC_FEATURE
<222> LOCATION: (56)..(56)
<223> OTHER INFORMATION: Xaa7 is serine (Ser), alanine (Ala), or
      aspartic acid (Asp)

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Xaa Met Xaa Trp Val Arg Gln Ala Pro Xaa Gln Gly Leu Glu Trp Met
            35                  40                  45

Gly Met Phe Xaa Pro Xaa Xaa Xaa Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Met Phe Asp Pro Ser Asn Ser Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Met Phe Glu Pro Ser Asn Ala Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Arg Gln Gly Leu Glu Trp Met
        35                  40                  45

Gly Met Phe Glu Pro Ser Asn Ala Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120
```

```
<210> SEQ ID NO 19
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 19
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Tyr Trp Val Arg Gln Ala Pro Arg Gln Gly Leu Glu Trp Met
        35                  40                  45

Gly Met Phe His Pro Ser Asn Ala Val Thr Arg Leu Asn Gln Lys Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

```
<210> SEQ ID NO 20
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 20
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Arg Gln Gly Leu Glu Trp Met
        35                  40                  45

Gly Met Phe His Pro Ser Asn Ala Val Thr Arg Leu Asn Gln Lys Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

```
<210> SEQ ID NO 21
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 21
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Asn Tyr
            20                  25                  30

Tyr Met Asn Trp Val Arg Gln Ala Pro Arg Gln Gly Leu Glu Trp Met
            35                  40                  45

Gly Met Phe His Pro Thr Gly Asp Val Thr Arg Leu Asn Gln Lys Phe
 50                      55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Thr Ser Met Ile Ile Gly Gly Phe Ala Tyr Trp Gly Gln
            100                 105                 110

Gly Thr Leu Val Thr Val Ser Ser
            115                 120

<210> SEQ ID NO 22
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Trp Met Asn Trp Val Arg Gln Ala Pro Arg Gln Gly Leu Glu Trp Met
            35                  40                  45

Gly Met Phe His Pro Thr Gly Asp Val Thr Arg Leu Asn Gln Lys Phe
 50                      55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Thr Ser Met Ile Ile Gly Gly Phe Ala Tyr Trp Gly Gln
            100                 105                 110

Gly Thr Leu Val Thr Val Ser Ser
            115                 120

<210> SEQ ID NO 23
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 23

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Tyr Met Asn Trp Val Arg Gln Ala Pro Arg Gln Gly Leu Glu Trp Met
            35                  40                  45

Gly Met Phe His Pro Tyr Gly Asp Val Thr Arg Leu Asn Gln Lys Phe
 50                      55                  60

Lys Asp Arg Val Thr Met Thr Arg Asp Thr Ser Thr Ser Thr Val Tyr
```

```
                 65                  70                  75                  80
Met Glu Leu Ser Ser Leu Arg Ser Glu Asp Thr Ala Val Tyr Tyr Cys
                    85                  90                  95

Ala Arg Thr Thr Ser Met Ile Ile Gly Gly Phe Ala Tyr Trp Gly Gln
                100                 105                 110

Gly Thr Leu Val Thr Val Ser Ser
            115                 120

<210> SEQ ID NO 24
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met Asn Trp Val Arg Gln Ala Pro Arg Gln Gly Leu Glu Trp Met
            35                  40                  45

Gly Met Phe His Pro Tyr Gly Asp Val Thr Arg Leu Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Thr Thr Ser Met Ile Ile Gly Gly Phe Ala Tyr Trp Gly Gln
                100                 105                 110

Gly Thr Leu Val Thr Val Ser Ser
            115                 120

<210> SEQ ID NO 25
<211> LENGTH: 117
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa1 is glutamine (Gln) or aspartic acid (Asp)
<220> FEATURE:
<221> NAME/KEY: MISC_FEATURE
<222> LOCATION: (4)..(4)
<223> OTHER INFORMATION: Xaa2 is leucine (Leu) or phenylalanine (Phe)
<220> FEATURE:
<221> NAME/KEY: MISC_FEATURE
<222> LOCATION: (25)..(25)
<223> OTHER INFORMATION: Xaa3 is threonine (Thr) or serine (Ser)
<220> FEATURE:
<221> NAME/KEY: MISC_FEATURE
<222> LOCATION: (41)..(41)
<223> OTHER INFORMATION: Xaa4 is proline (Pro) or phenylalanine (Phe)
<220> FEATURE:
<221> NAME/KEY: MISC_FEATURE
<222> LOCATION: (44)..(44)
<223> OTHER INFORMATION: Xaa5 is lysine (Lys) or asparagine (Asn)
<220> FEATURE:
<221> NAME/KEY: MISC_FEATURE
<222> LOCATION: (45)..(45)
<223> OTHER INFORMATION: Xaa6 is glycine (Gly) or lysine (Lys)
<220> FEATURE:
<221> NAME/KEY: MISC_FEATURE
<222> LOCATION: (71)..(71)
```

<223> OTHER INFORMATION: Xaa7 is serine (Ser) or threonine (Thr)
<220> FEATURE:
<221> NAME/KEY: MISC_FEATURE
<222> LOCATION: (72)..(72)
<223> OTHER INFORMATION: Xaa8 is valine (Val) or arginine (Arg)
<220> FEATURE:
<221> NAME/KEY: MISC_FEATURE
<222> LOCATION: (95)..(95)
<223> OTHER INFORMATION: Xaa9 is tyrosine (Tyr) or phenylalanine (Phe)

<400> SEQUENCE: 25

Xaa Val Gln Xaa Gln Glu Ser Gly Pro Gly Leu Val Lys Pro Ser Gln
1               5                   10                  15

Thr Leu Ser Leu Thr Cys Thr Val Xaa Gly Tyr Ser Ile Thr Ser Asp
            20                  25                  30

Phe Ala Trp Asn Trp Ile Arg Gln Xaa Pro Gly Xaa Xaa Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Xaa Xaa Asp Thr Ser Lys Asn Gln Phe Ser
65                  70                  75                  80

Leu Lys Leu Ser Ser Val Thr Ala Ala Asp Thr Ala Val Tyr Xaa Cys
                85                  90                  95

Ala Ile Arg Gly Pro Tyr Ser Phe Thr Tyr Trp Gly Gln Gly Thr Leu
            100                 105                 110

Val Thr Val Ser Ser
            115

<210> SEQ ID NO 26
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ile Arg Gly Pro Tyr Ser Phe Thr Tyr Trp Gly Gln Gly Thr Leu
            100                 105                 110

Val Thr Val Ser Ser
            115

<210> SEQ ID NO 27
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 27

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Arg Asp Thr Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115

<210> SEQ ID NO 28
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ile Arg Gly Pro Tyr Ser Phe Thr Tyr Trp Gly Gln Gly Thr Leu
            100                 105                 110

Val Thr Val Ser Ser
        115

<210> SEQ ID NO 29
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 29

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Asn Lys Leu Glu Trp
        35                  40                  45

Ile Gly Tyr Ile Ser Tyr Ser Gly Asp Thr Asn Tyr Asn Pro Ser Leu

```
                50                  55                  60
Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Ala Ile Arg Gly Pro Tyr Ser Phe Thr Tyr Trp Gly Gln Gly Thr Leu
                100                 105                 110

Val Thr Val Ser Ser
            115

<210> SEQ ID NO 30
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 30

Gln Val Gln Phe Gln Glu Ser Gly Pro Gly Leu Val Lys Pro Ser Gln
 1               5                  10                  15

Thr Leu Ser Leu Thr Cys Thr Val Ser Gly Tyr Ser Ile Thr Ser Asp
                20                  25                  30

Phe Ala Trp Asn Trp Ile Arg Gln Phe Pro Gly Lys Gly Leu Glu Trp
             35                  40                  45

Ile Gly Tyr Ile Ser Tyr Ser Gly Asp Thr Asn Tyr Asn Pro Ser Leu
         50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Ala Ile Arg Gly Pro Tyr Ser Phe Thr Tyr Trp Gly Gln Gly Thr Leu
                100                 105                 110

Val Thr Val Ser Ser
            115

<210> SEQ ID NO 31
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 31

Gln Val Gln Phe Gln Glu Ser Gly Pro Gly Leu Val Lys Pro Ser Gln
 1               5                  10                  15

Thr Leu Ser Leu Thr Cys Thr Val Ser Gly Tyr Ser Ile Thr Ser Asp
                20                  25                  30

Phe Ala Trp Asn Trp Ile Arg Gln Phe Pro Gly Asn Lys Leu Glu Trp
             35                  40                  45

Ile Gly Tyr Ile Ser Tyr Ser Gly Asp Thr Asn Tyr Asn Pro Ser Leu
         50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Ala Ile Arg Gly Pro Tyr Ser Phe Thr Tyr Trp Gly Gln Gly Thr Leu
                100                 105                 110
```

```
Val Thr Val Ser Ser
        115
```

<210> SEQ ID NO 32
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 32

```
Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Thr Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115
```

<210> SEQ ID NO 33
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 33

```
Gln Val Gln Leu Gln Gln Ser Gly Pro Glu Leu Val Lys Pro Gly Ala
1               5                   10                  15

Leu Val Lys Ile Ser Cys Lys Ala Ser Gly Phe Thr Phe Thr Ser Tyr
            20                  25                  30

Asp Ile Asn Trp Val Arg Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asn Ser Ala Val Tyr Phe Cys
                85                  90                  95

Thr Arg Ser Phe Tyr Thr Met Asp Tyr Trp Gly Gln Gly Thr Ser Val
            100                 105                 110

Thr Val Ser Ser
        115
```

<210> SEQ ID NO 34
<211> LENGTH: 120
<212> TYPE: PRT
<213> ORGANISM: Artificial Sequence
<220> FEATURE:
<223> OTHER INFORMATION: Synthetic Sequence -continued

```
<400> SEQUENCE: 34

Gln Val Gln Leu Gln Gln Ser Gly Pro Glu Leu Val Arg Pro Gly Ala
1               5                   10                  15

Ser Val Arg Met Ser Cys Lys Ala Ser Asp Tyr Thr Phe Thr Asn Tyr
            20                  25                  30

Trp Met His Trp Val Lys Gln Arg Pro Gly Gln Gly Leu Glu Trp Ile
        35                  40                  45

Gly Met Phe Asp Pro Ser Asn Ser Val Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Ile Gln Phe Ser Ser Leu Thr Phe Glu Asp Ser Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120

<210> SEQ ID NO 35
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 35

Asp Val Gln Phe Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asp Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Ile Arg Gly Pro Tyr Ser Phe Thr Tyr Trp Gly Pro Gly Thr Leu
            100                 105                 110

Val Thr Val Ser Ser
        115

<210> SEQ ID NO 36
<211> LENGTH: 112
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (34)..(34)
<223> OTHER INFORMATION: Xaa1 is glycine (Gly) or alanine (Ala)
<220> FEATURE:
<221> NAME/KEY: MISC_FEATURE
<222> LOCATION: (41)..(41)
<223> OTHER INFORMATION: Xaa2 is phenylalanine (Phe) or tyrosine (Tyr)
<220> FEATURE:
<221> NAME/KEY: MISC_FEATURE
<222> LOCATION: (54)..(54)
<223> OTHER INFORMATION: Xaa3 is tyrosine (Tyr) or serine (Ser)
```

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Xaa Asn Thr Tyr Leu Tyr Trp Xaa Leu Gln Lys Pro Gly Gln Ser
        35                  40                  45

Pro Gln Leu Leu Ile Xaa Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Ser Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110
```

<210> SEQ ID NO 39
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 39

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Asn Thr Tyr Leu Tyr Trp Phe Leu Gln Lys Pro Gly Gln Ser
        35                  40                  45

Pro Gln Leu Leu Ile Ser Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110
```

<210> SEQ ID NO 40
<211> LENGTH: 112
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (32)..(32)
<223> OTHER INFORMATION: Xaa1 is serine (Ser) or arginine (Arg)
<220> FEATURE:
<221> NAME/KEY: MISC_FEATURE
<222> LOCATION: (34)..(34)
<223> OTHER INFORMATION: Xaa2 is glycine (Gly) or alanine (Ala)
<220> FEATURE:
<221> NAME/KEY: MISC_FEATURE
<222> LOCATION: (43)..(43)
<223> OTHER INFORMATION: Xaa3 is glutamine (Gln) or histidine (His)

<400> SEQUENCE: 40

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Xaa
            20                  25                  30

Asn Xaa Ile Thr Tyr Phe Tyr Trp Tyr Leu Xaa Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
```

-continued

```
                       100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Gly Ile Thr Tyr Phe Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Ala Ile Thr Tyr Phe Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 43

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Arg
            20                  25                  30
```

```
Asn Ala Ile Thr Tyr Phe Tyr Trp Tyr Leu Gln Lys Pro Gly Gln Pro
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 44

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Arg
            20                  25                  30

Asn Ala Ile Thr Tyr Phe Tyr Trp Tyr Leu His Lys Pro Gly Gln Pro
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 45
<211> LENGTH: 107
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (64)..(64)
<223> OTHER INFORMATION: Xaa1 is serine (Ser) or proline (Pro)
<220> FEATURE:
<221> NAME/KEY: MISC_FEATURE
<222> LOCATION: (71)..(71)
<223> OTHER INFORMATION: Xaa2 is phenylalanine (Phe) or tyrosine (Tyr)

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Xaa
    50                  55                  60

Ser Gly Ser Gly Thr Asp Xaa Thr Phe Thr Ile Ser Ser Leu Gln Pro
65                  70                  75                  80
```

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
                100                 105

<210> SEQ ID NO 46
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
                100                 105

<210> SEQ ID NO 47
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Pro
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
                100                 105

<210> SEQ ID NO 48
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 48

```
Asp Ile Val Met Thr Gln Ala Ala Pro Ser Val Pro Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
            35                  40                  45

Pro Gln Leu Leu Ile Ser Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110
```

<210> SEQ ID NO 49
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 49

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Tyr Trp Tyr Leu Gln Arg Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 50
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 50

```
Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile Asn Asn Tyr
            20                  25                  30

Leu Asn Trp Tyr Gln Gln Lys Pro Asp Gly Thr Ile Arg Leu Leu Ile
            35                  40                  45

Tyr Tyr Thr Ser Arg Leu His Ser Gly Val Pro Ser Arg Phe Ser Pro
        50                  55                  60

Asn Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly His Thr Leu Pro Trp
                85                  90                  95
```

Thr Phe Gly Gly Gly Thr Lys Leu Glu Ile Lys
                100                 105

<210> SEQ ID NO 51
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 51

Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 52

Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser Ala
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 53

Asp Leu Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
            85                  90                  95

Ala Ile Arg Gly Pro Tyr Ser Phe Thr Tyr Trp Gly Gln Gly Thr Leu
                100                 105                 110

Val Thr Val Ser Ser Ala
            115

<210> SEQ ID NO 54
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 54

Asp Leu Gln Phe Gln Glu Ser Gly Pro Gly Leu Val Lys Pro Ser Gln
1               5                   10                  15

Thr Leu Ser Leu Thr Cys Thr Val Ser Arg Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
            85                  90                  95

Ala Ile Arg Gly Pro Tyr Ser Phe Thr Tyr Trp Gly Gln Gly Thr Leu
                100                 105                 110

Val Thr Val Ser Ser Ala
            115

<210> SEQ ID NO 55
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Asn Asn Tyr
            20                  25                  30

Leu Asn Trp Tyr Gln Gln Lys Pro Gly Lys Ala Pro Lys Leu Leu Ile
        35                  40                  45

```
Tyr Tyr Thr Ser Met Leu His Ser Gly Val Pro Ser Arg Phe Ser Pro
 50                  55                  60

Ser Gly Ser Gly Asn Asp Tyr Thr Phe Thr Ile Ser Ser Leu Gln Pro
 65                  70                  75                  80

Glu Asp Ile Ala Thr Tyr Tyr Cys Gln Gln Gly His Thr Leu Pro Trp
                 85                  90                  95

Thr Phe Gly Gly Gly Thr Lys Val Glu Ile Lys Arg Thr
                100                 105
```

```
<210> SEQ ID NO 56
<211> LENGTH: 116
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: Xaa1 is leucine (Leu) or phenylalanine (Phe)
<220> FEATURE:
<221> NAME/KEY: MISC_FEATURE
<222> LOCATION: (5)..(5)
<223> OTHER INFORMATION: Xaa2 is valine (Val), methionine (Met), or
      leucine (Leu)
<220> FEATURE:
<221> NAME/KEY: MISC_FEATURE
<222> LOCATION: (44)..(44)
<223> OTHER INFORMATION: Xaa3 is arginine (Arg) or glycine (Gly)
<220> FEATURE:
<221> NAME/KEY: MISC_FEATURE
<222> LOCATION: (56)..(56)
<223> OTHER INFORMATION: Xaa4 is glycine (Gly), serine (Ser), or alanine
      (Ala)
<220> FEATURE:
<221> NAME/KEY: MISC_FEATURE
<222> LOCATION: (72)..(72)
<223> OTHER INFORMATION: Xaa5 is arginine (Arg) or alanine (Ala)
<220> FEATURE:
<221> NAME/KEY: MISC_FEATURE
<222> LOCATION: (74)..(74)
<223> OTHER INFORMATION: Xaa6 is threonine (Thr) or lysine (Lys)
<220> FEATURE:
<221> NAME/KEY: MISC_FEATURE
<222> LOCATION: (77)..(77)
<223> OTHER INFORMATION: Xaa7 is serine (Ser) or asparagine (Asn)
<220> FEATURE:
<221> NAME/KEY: MISC_FEATURE
<222> LOCATION: (84)..(84)
<223> OTHER INFORMATION: Xaa8 is serine (Ser) or alanine (Ala)
<220> FEATURE:
<221> NAME/KEY: MISC_FEATURE
<222> LOCATION: (95)..(95)
<223> OTHER INFORMATION: Xaa9 is tyrosine (Tyr) or phenylalanine (Phe)

<400> SEQUENCE: 56

Gln Val Gln Xaa Xaa Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                 20                  25                  30

Asp Ile Asn Trp Val Arg Gln Ala Pro Gly Gln Xaa Leu Glu Trp Met
                 35                  40                  45

Gly Trp Ile Tyr Pro Gly Asp Xaa Ser Thr Lys Tyr Asn Glu Lys Phe
 50                  55                  60

Lys Gly Arg Val Thr Ile Thr Xaa Asp Xaa Ser Ala Xaa Thr Ala Tyr
 65                  70                  75                  80

Met Glu Leu Xaa Ser Leu Arg Ser Glu Asp Thr Ala Val Tyr Xaa Cys
                 85                  90                  95
```

```
Thr Arg Ser Phe Tyr Thr Met Asp Tyr Trp Gly Gln Gly Thr Thr Val
            100                 105                 110

Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa1 is glutamine (Gln) or aspartic acid (Asp)
<220> FEATURE:
<221> NAME/KEY: MISC_FEATURE
<222> LOCATION: (2)..(2)
<223> OTHER INFORMATION: Xaa2 is valine (Val) or leucine (Leu)
<220> FEATURE:
<221> NAME/KEY: MISC_FEATURE
<222> LOCATION: (4)..(4)
<223> OTHER INFORMATION: Xaa3 is leucine (Leu) or phenylalanine (Phe)
<220> FEATURE:
<221> NAME/KEY: MISC_FEATURE
<222> LOCATION: (25)..(25)
<223> OTHER INFORMATION: Xaa4 is threonine (Thr) or serine (Ser)
<220> FEATURE:
<221> NAME/KEY: MISC_FEATURE
<222> LOCATION: (26)..(26)
<223> OTHER INFORMATION: Xaa5 is glycine (Gly) or arginine (Arg)
<220> FEATURE:
<221> NAME/KEY: MISC_FEATURE
<222> LOCATION: (31)..(31)
<223> OTHER INFORMATION: Xaa6 serine (Ser) or alanine (Ala)
<220> FEATURE:
<221> NAME/KEY: MISC_FEATURE
<222> LOCATION: (41)..(41)
<223> OTHER INFORMATION: Xaa7 is proline (Pro) or phenylalanine (Phe)
<220> FEATURE:
<221> NAME/KEY: MISC_FEATURE
<222> LOCATION: (44)..(44)
<223> OTHER INFORMATION: Xaa8 is lysine (Lys) or asparagine (Asn)
<220> FEATURE:
<221> NAME/KEY: MISC_FEATURE
<222> LOCATION: (45)..(45)
<223> OTHER INFORMATION: Xaa9 is glycine (Gly) or lysine (Lys)
<220> FEATURE:
<221> NAME/KEY: MISC_FEATURE
<222> LOCATION: (71)..(71)
<223> OTHER INFORMATION: Xaa10 is serine (Ser) or threonine (Thr)
<220> FEATURE:
<221> NAME/KEY: MISC_FEATURE
<222> LOCATION: (72)..(72)
<223> OTHER INFORMATION: Xaa11 is valine (Val) or arginine (Arg)
<220> FEATURE:
<221> NAME/KEY: MISC_FEATURE
<222> LOCATION: (93)..(93)
<223> OTHER INFORMATION: Xaa12 is threonine (Thr) or valine (Val)
<220> FEATURE:
<221> NAME/KEY: MISC_FEATURE
<222> LOCATION: (95)..(95)
<223> OTHER INFORMATION: Xaa13 is tyrosine (Tyr) or phenylalanine (Phe)
<220> FEATURE:
<221> NAME/KEY: MISC_FEATURE
<222> LOCATION: (118)..(118)
<223> OTHER INFORMATION: Xaa14 is is alanine (Ala) or absent

<400> SEQUENCE: 57

Xaa Xaa Gln Xaa Gln Glu Ser Gly Pro Gly Leu Val Lys Pro Ser Gln
1               5                   10                  15

Thr Leu Ser Leu Thr Cys Thr Val Xaa Xaa Tyr Ser Ile Thr Xaa Asp
            20                  25                  30

Phe Ala Trp Asn Trp Ile Arg Gln Xaa Pro Gly Xaa Xaa Leu Glu Trp
```

-continued

```
                35                  40                  45
Ile Gly Tyr Ile Ser Tyr Ser Gly Asp Thr Asn Tyr Asn Pro Ser Leu
    50                  55                  60
Lys Ser Arg Val Thr Ile Xaa Xaa Asp Thr Ser Lys Asn Gln Phe Ser
 65                  70                  75                  80
Leu Lys Leu Ser Ser Val Thr Ala Ala Asp Thr Ala Xaa Tyr Xaa Cys
                 85                  90                  95
Ala Ile Arg Gly Pro Tyr Ser Phe Thr Tyr Trp Gly Gln Gly Thr Leu
            100                 105                 110
Val Thr Val Ser Ser Xaa
            115

<210> SEQ ID NO 58
<211> LENGTH: 109
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (28)..(28)
<223> OTHER INFORMATION: Xaa1 is aspartic acid (Asp) or tryptophan (Trp)
<220> FEATURE:
<221> NAME/KEY: MISC_FEATURE
<222> LOCATION: (53)..(53)
<223> OTHER INFORMATION: Xaa2 is arginine (Arg) or methionine (Met)
<220> FEATURE:
<221> NAME/KEY: MISC_FEATURE
<222> LOCATION: (64)..(64)
<223> OTHER INFORMATION: Xaa3 is glycine (Gly), serine (Ser) or proline
      (Pro)
<220> FEATURE:
<221> NAME/KEY: MISC_FEATURE
<222> LOCATION: (69)..(69)
<223> OTHER INFORMATION: Xaa4 is threonine (Thr) or asparagine (Asn)
<220> FEATURE:
<221> NAME/KEY: MISC_FEATURE
<222> LOCATION: (71)..(71)
<223> OTHER INFORMATION: Xaa5 is phenylalanine (Phe) or tyrosine (Tyr)
<220> FEATURE:
<221> NAME/KEY: MISC_FEATURE
<222> LOCATION: (108)..(108)
<223> OTHER INFORMATION: Xaa6 is arginine (Arg) or absent
<220> FEATURE:
<221> NAME/KEY: MISC_FEATURE
<222> LOCATION: (109)..(109)
<223> OTHER INFORMATION: Xaa7 is threonine (Thr) or absent

<400> SEQUENCE: 58

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Xaa Ile Asn Asn Tyr
             20                  25                  30
Leu Asn Trp Tyr Gln Gln Lys Pro Gly Lys Ala Pro Lys Leu Leu Ile
         35                  40                  45
Tyr Tyr Thr Ser Xaa Leu His Ser Gly Val Pro Ser Arg Phe Ser Xaa
     50                  55                  60
Ser Gly Ser Gly Xaa Asp Xaa Thr Phe Thr Ile Ser Ser Leu Gln Pro
 65                  70                  75                  80
Glu Asp Ile Ala Thr Tyr Tyr Cys Gln Gln Gly His Thr Leu Pro Trp
                 85                  90                  95
Thr Phe Gly Gly Gly Thr Lys Val Glu Ile Lys Xaa Xaa
            100                 105
```